United States Patent
Yang et al.

(10) Patent No.: US 12,104,205 B2
(45) Date of Patent: *Oct. 1, 2024

(54) PCR PRIMER PAIR AND APPLICATION THEREOF

(71) Applicant: MGI Tech Co., Ltd., Shenzhen (CN)

(72) Inventors: Lin Yang, Shenzhen (CN); Haojun Jiang, Shenzhen (CN); Peng Zeng, Shenzhen (CN); Xuehan Zhuang, Shenzhen (CN); Ya Gao, Shenzhen (CN); Yanyan Zhang, Shenzhen (CN); Hui Jiang, Shenzhen (CN); Jing Guo, Shenzhen (CN); Fang Chen, Shenzhen (CN); Xun Xu, Shenzhen (CN)

(*) Notice: Subject to any disclaimer, the term of this patent is extended or adjusted under 35 U.S.C. 154(b) by 704 days.

This patent is subject to a terminal disclaimer.

(21) Appl. No.: 16/624,782

(22) PCT Filed: Jun. 20, 2017

(86) PCT No.: PCT/CN2017/089199
§ 371 (c)(1),
(2) Date: Dec. 19, 2019

(87) PCT Pub. No.: WO2018/232598
PCT Pub. Date: Dec. 27, 2018

(65) Prior Publication Data
US 2020/0216874 A1    Jul. 9, 2020

(51) Int. Cl.
C12Q 1/68      (2018.01)
C12Q 1/6818    (2018.01)
C12Q 1/6853    (2018.01)
C12Q 1/686     (2018.01)

(52) U.S. Cl.
CPC .......... *C12Q 1/686* (2013.01); *C12Q 1/6818* (2013.01); *C12Q 1/6853* (2013.01); *C12Q 2600/16* (2013.01)

(58) Field of Classification Search
None
See application file for complete search history.

(56) References Cited

U.S. PATENT DOCUMENTS

2006/0292611 A1   12/2006  Berka et al.
2007/0172824 A1*   7/2007  Chun ............... C12Q 1/686
                                               435/6.11
2009/0130720 A1    5/2009  Nelson et al.
2014/0113332 A1*   4/2014  Betts .............. C12Y 207/07007
                                               435/91.5
2016/0026758 A1*   1/2016  Jabara ............. C12Q 1/6874
                                               506/4

FOREIGN PATENT DOCUMENTS

CN      101809170 A       8/2010
CN      103820561 B       4/2016
WO   WO-2015117040 A1 *   8/2015   ........... C12Q 1/6855
WO      2016181128 A1    11/2016

OTHER PUBLICATIONS

Search Report issued for EP patent application serial No. 17915187.3, dated Dec. 7, 2020.
Korfhage, C. "Clonal rolling circle amplification for on-chip DNA cluster generation" (2017) Biology Methods and Protocols, vol. 2, No. 1.
Zong, C. et al. "Genome-Wide Detection of Single Nucleotide and Copy Number Variations of a Single Human Cell", Science, 338(6114), Dec. 21, 2012 (Dec. 21, 2012), pp. 1622-1626.
International Search Report and Written Opinion issued for PCT/CN2017/089199, dated Apr. 3, 2018.

* cited by examiner

*Primary Examiner* — Suryaprabha Chunduru
(74) *Attorney, Agent, or Firm* — Z. Peter Sawicki; Amanda M. Prose; Westman, Champlin & Koehler PA

(57) ABSTRACT

Provided are a PCR primer pair and an application thereof. The PCR primer pair comprises a first primer and a second primer, wherein the first primer comprises a first specific sequence, a first random sequence, and a first universal sequence, the first specific sequence is located at the 3' end of the first primer, the first random sequence is located at the 5' end of the first primer, and the first universal sequence is located between the first specific sequence and the first random sequence; the second primer comprises a second specific sequence, a second random sequence, and a second universal sequence, the second specific sequence is located at the 3' end of the second primer, the second random sequence is located at the 5' end of the second primer, and the second universal sequence is located between the second specific sequence and the second random sequence, wherein the first random sequence and the second random sequence are inversely complementary.

10 Claims, 6 Drawing Sheets

Specification includes a Sequence Listing.

SEQUENCE LISTING

```
<160> NUMBER OF SEQ ID NOS: 136

<210> SEQ ID NO 1
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 1
gggggcggtt gggggcgcct tggcctccga cttccnnnnn gtatatttct ctttcacttc    60
ct                                                                   62

<210> SEQ ID NO 2
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 2
ccggccggat gcgccgccct tggcctccga cttccnnnnn gggcaacttc tctgtttctt    60
tt                                                                   62

<210> SEQ ID NO 3
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
```

-continued

<223> OTHER INFORMATION: n is a, c, g, or t

<400> SEQUENCE: 3
gcgccgcgat gcggcccct tggcctccga cttccnnnnn atgcatctat tacttttaca    60
tt                                                                  62

<210> SEQ ID NO 4
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 4
cggggcggtt gcggcgcgct tggcctccga cttccnnnnn aataatcacc ctgttgtttg    60
tt                                                                  62

<210> SEQ ID NO 5
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 5
cgggccccat ccggggccct tggcctccga cttccnnnnn actgcctcat ctctcaccat    60
cc                                                                  62

<210> SEQ ID NO 6
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 6
ggggcgcgtt cggggccct tggcctccga cttccnnnnn cggagcgagc tcttcgggga    60
gc                                                                  62

<210> SEQ ID NO 7
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 7
gggccccgtt ggccgcgcct tggcctccga cttccnnnnn tctgaagtct ttcatctgcc    60
tt                                                                  62

<210> SEQ ID NO 8
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 8
ggcgcccgtt cgggccggct tggcctccga cttccnnnnn ctgaaaacag gacggacctc    60
ca                                                                  62

<210> SEQ ID NO 9
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 9
gcggggccat cggccggct tggcctccga cttccnnnnn gacgggtttc ctcttcctcc    60
tc                                                                  62

<210> SEQ ID NO 10
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 10
cggcggcctt gggccgggct tggcctccga cttccnnnnn ctctgagtgc atacagtgcc    60
ac                                                                  62

<210> SEQ ID NO 11
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 11
gccgcgcctt ccggcccgct tggcctccga cttccnnnnn actgtttttt ctcattcctt    60
cc                                                                  62

<210> SEQ ID NO 12
<211> LENGTH: 62
<212> TYPE: DNA
<213> ORGANISM: Artificial
<220> FEATURE:

```
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 12
gcgccgcgat gcccggggct tggcctccga cttccnnnnn gcccaaagtt ccgtgagttg    60
at                                                                  62

<210> SEQ ID NO 13
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 13
ccgcggggta gcgcccggct tggcctccga cttccnnnnn acgtcttcct tctctctctg    60
tc                                                                  62

<210> SEQ ID NO 14
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 14
ggccggcgtt gcgcccggct tggcctccga cttccnnnnn aaagttaaaa ttcccgtcgc    60
ta                                                                  62

<210> SEQ ID NO 15
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 15
gccccgcgtt gggccggcct tggcctccga cttccnnnnn taaccttccc tcatttcctc    60
ct                                                                  62

<210> SEQ ID NO 16
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 16
```
gcgcgccgtt cgcgcgcgct tggcctccga cttccnnnnn gacagcttct tgcagcgata    60
ca    62

<210> SEQ ID NO 17
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 17
cgggggggta cccgcgccct tggcctccga cttccnnnnn ccttcctttc atgctctctt    60
cc    62

<210> SEQ ID NO 18
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 18
cgcgccggtt ggcgccccct tggcctccga cttccnnnnn gctcgtgcgt ccgagcctgt    60
gg    62

<210> SEQ ID NO 19
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 19
gcgcgcgcta cggccgggct tggcctccga cttccnnnnn cacagggaac ctttgctctt    60
tt    62

<210> SEQ ID NO 20
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 20 cggggggta gggcggccct tggcctccga cttccnnnnn agtgctccgg gcgctgccgt    60
gg    62

<210> SEQ ID NO 21

```
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 21
gcgggcgctt gggcgccgct tggcctccga cttccnnnnn tgtctctgtg ttcttgtccc    60
cc                                                                  62

<210> SEQ ID NO 22
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 22
cgggggccat ggggcgccct tggcctccga cttccnnnnn ggagaagctc ccaaccaagc    60
tc                                                                  62

<210> SEQ ID NO 23
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 23
gccgcggctt gcccggcgct tggcctccga cttccnnnnn aatacacgtc tctcttatct    60
ct                                                                  62

<210> SEQ ID NO 24
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 24
cggcgcgcat cgcgcgggct tggcctccga cttccnnnnn aatttaaaga ctcactctcc    60
at                                                                  62

<210> SEQ ID NO 25
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
```

<222> LOCATION: (36)..(40)
<223> OTHER INFORMATION: n is a, c, g, or t

<400> SEQUENCE: 25 gcccccgtt cccgggggct tggcctccga cttccnnnnn tgctgtgacc cactctgtct    60
cc                                                                 62

<210> SEQ ID NO 26
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 26
ccgcgcgctt ccgcggcgct tggcctccga cttccnnnnn gtctgccatg ccttgtgctc    60
cc                                                                 62

<210> SEQ ID NO 27
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 27
cccccggctt cgcgcgcgct tggcctccga cttccnnnnn cggagcccag ggactgcgtc    60
tc                                                                 62

<210> SEQ ID NO 28
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 28
gcggcgggtt ccgccgggct tggcctccga cttccnnnnn ctcaccgcag ttccattctc    60
cc                                                                 62

<210> SEQ ID NO 29
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 29
cggcgcgcta cggggcggct tggcctccga cttccnnnnn gccgtgcggt tcagcaacaa    60

```
cc                                                                 62

<210> SEQ ID NO 30
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 30
cggccggcat cgcgcccct tggcctccga cttccnnnnn agagcatcca gtggcgggac   60
at                                                                 62

<210> SEQ ID NO 31
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 31 gccgcccta cggccgccct tggcctccga cttccnnnnn cccagcgtgt cctctctcct   60
cc                                                                 62

<210> SEQ ID NO 32
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 32 cgcccccat ggggcggcct tggcctccga cttccnnnnn ccgagacgaa gccacgtgca   60
ag                                                                 62

<210> SEQ ID NO 33
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 33
gcgccggcta cccgcgggct tggcctccga cttccnnnnn atgctctaca accccaccac   60
gt                                                                 62

<210> SEQ ID NO 34
<211> LENGTH: 62
<212> TYPE: DNA
<213> ORGANISM: Artificial
```

```
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 34
ccgccgcctt cccggccgct tggcctccga cttccnnnnn ttccttgttc ctccacctca    60
tt                                                                  62

<210> SEQ ID NO 35
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 35
cggcgccgta cggccgccct tggcctccga cttccnnnnn ccatcgccac tgggatggtg    60
gg                                                                  62

<210> SEQ ID NO 36
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 36
gccggcgcta cggcgcgcct tggcctccga cttccnnnnn ggtggtggcc ctggggatcg    60
gc                                                                  62

<210> SEQ ID NO 37
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 37
cgcgcggcta cgccgcccct tggcctccga cttccnnnnn cttcttttct tgcttcatcc    60
tc                                                                  62

<210> SEQ ID NO 38
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t
```

<400> SEQUENCE: 38
cgcgcggcat cggccgccct tggcctccga cttccnnnnn gagttgatga cctttggatc    60
ca                                                                  62

<210> SEQ ID NO 39
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 39
cgccggccat ggccccgcct tggcctccga cttccnnnnn ctgccagcga gatctcctcc    60
at                                                                  62

<210> SEQ ID NO 40
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 40
gccgggccta ccggggccct tggcctccga cttccnnnnn atgtgatatc tgtcttttc    60 tt                                                                  62

<210> SEQ ID NO 41
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 41 cgcccccat ccccgcgcct tggcctccga cttccnnnnn caagctcacg cagttgggca    60
ct                                                                  62

<210> SEQ ID NO 42
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 42
cgcccgggtt ggccggccct tggcctccga cttccnnnnn agcctccaga ggatgttcaa    60
ta                                                                  62

```
<210> SEQ ID NO 43
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 43
cgggcccgtt gggcggcgct tggcctccga cttccnnnnn tcacagcagg gtcttctctg      60
tt                                                                    62

<210> SEQ ID NO 44
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 44
gggcgcggtt ccgcccgcct tggcctccga cttccnnnnn accgtcgctt ggtgcaccgc      60
ga                                                                    62

<210> SEQ ID NO 45
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 45
cgggcccgtt ccgcgcgcct tggcctccga cttccnnnnn actggtgaaa acaccgcagc      60
at                                                                    62

<210> SEQ ID NO 46
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 46
gcccgcgcta ggcgccggct tggcctccga cttccnnnnn gaacattttt ctccaccttg      60
gt                                                                    62

<210> SEQ ID NO 47
<211> LENGTH: 62
<212> TYPE: DNA
<213> ORGANISM: Artificial
<220> FEATURE:
<223> OTHER INFORMATION: Primer
<220> FEATURE:
```

<221> NAME/KEY: misc_feature
<222> LOCATION: (36)..(40)
<223> OTHER INFORMATION: n is a, c, g, or t

<400> SEQUENCE: 47
gcgcgccgat gcccgcccct tggcctccga cttccnnnnn agtgtgccca ctacattgac    60
gg                                                                  62

<210> SEQ ID NO 48
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 48 gcggccccctt gccccggcct tggcctccga cttccnnnnn ctgcccggca ggagtcatgg    60
ga                                                                  62

<210> SEQ ID NO 49
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 49
gccgcggcat cgcccgggct tggcctccga cttccnnnnn taatagcctc aaaatctctg    60
ca                                                                  62

<210> SEQ ID NO 50
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 50
gcgcccgctt cccccccgct tggcctccga cttccnnnnn tgccaagtcc tacagactcc    60
aa                                                                  62

<210> SEQ ID NO 51
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 51
ggcgcgcctt ccccgggcct tggcctccga cttccnnnnn ggatgaagaa gacatggacg    60

```
ac                                                                62
```

<210> SEQ ID NO 52
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 52

```
cccccccgcat gccggcccct tggcctccga cttccnnnnn cacgcattta tgttttctct    60
tc                                                                    62
```

<210> SEQ ID NO 53
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 53

```
gcgccggcat cgccggccct tggcctccga cttccnnnnn ccctcaacac agtggagcga    60
at                                                                    62
```

<210> SEQ ID NO 54
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 54

```
ccccggcgta cggcgcccct tggcctccga cttccnnnnn gatcatcaga ggaaatatgt    60
ac                                                                    62
```

<210> SEQ ID NO 55
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 55

```
cccggcgctt ccgccggcct tggcctccga cttccnnnnn actgacgtgc ctctccctcc    60
ct                                                                    62
```

<210> SEQ ID NO 56
<211> LENGTH: 62
<212> TYPE: DNA

```
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 56
cgcgcggcta cgggcgggct tggcctccga cttccnnnnn acgtgtgccg cctgctgggc      60
at                                                                    62

<210> SEQ ID NO 57
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 57
gccgccggat gggcccgcct tggcctccga cttccnnnnn gcagctcatc acgcagctca      60
tg                                                                    62

<210> SEQ ID NO 58
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 58 cccggcccett ggggccgcct tggcctccga cttccnnnnn catgattttt cttctctcca     60
at                                                                    62

<210> SEQ ID NO 59
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 59 ggggccgtt ccccgccct tggcctccga cttccnnnnn ataacatcct tgggattacg        60
ct                                                                    62

<210> SEQ ID NO 60
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t
```

<400> SEQUENCE: 60
gcggggcgta ggcccgccct tggcctccga cttccnnnnn atggagatgt gataatttca    60
gg    62

<210> SEQ ID NO 61
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 61
gccgcgggtt ggggcgcgct tggcctccga cttccnnnnn cacctctgat ttctttccac    60
tt    62

<210> SEQ ID NO 62
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 62
ccccccccta cggcccggct tggcctccga cttccnnnnn tggctctgtg cagaatcctg    60
tc    62

<210> SEQ ID NO 63
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 63
cgggggccat ccccgcccct tggcctccga cttccnnnnn cccacactac caggaccccc    60
ac    62

<210> SEQ ID NO 64
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 64
ccggggcctt cgggggcgct tggcctccga cttccnnnnn ccagcccacc tgtgtcaaca    60
gc    62

<210> SEQ ID NO 65
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 65
gcgccgcgtt cggcgccgct tggcctccga cttccnnnnn ccaccaaatt agcctggaca    60
ac                                                                  62

<210> SEQ ID NO 66
<211> LENGTH: 62
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (36)..(40)
<223> OTHER INFORMATION: n is a, c, g, or t

<400> SEQUENCE: 66
ccgcggggta cgcgggggct tggcctccga cttccnnnnn gccaaatggc atctttaagg    60
gc                                                                  62

<210> SEQ ID NO 67
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 67
gcgcccccaa ccgcccsctg gctacgatcc gacttggnnn nngacacaga gctgtgaaca    60
ctta                                                                64

<210> SEQ ID NO 68
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 68
ggcggcgcat ccggccggtg gctacgatcc gacttggnnn nngcttataa ggtgttcata    60
cata                                                                64

<210> SEQ ID NO 69
<211> LENGTH: 64
<212> TYPE: DNA
<213> ORGANISM: Artificial
<220> FEATURE:
<223> OTHER INFORMATION: Primer

```
<220> FEATURE:
<221> NAME/KEY: misc_feature
<222> LOCATION: (38)..(42)
<223> OTHER INFORMATION: n is a, c, g, or t

<400> SEQUENCE: 69
ggggccgcat cgcggcgctg gctacgatcc gacttggnnn nntctgaggc tgttcactga    60
ctta                                                                 64

<210> SEQ ID NO 70
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 70
cgcgccgcaa ccgccccgtg gctacgatcc gacttggnnn nntcatgtga taattcagct    60
caaa                                                                 64

<210> SEQ ID NO 71
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 71
ggccccggat ggggcccgtg gctacgatcc gacttggnnn nnttagcatc aggattatga    60
ctca                                                                 64

<210> SEQ ID NO 72
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 72
ggcccccgaa cgcgcccctg gctacgatcc gacttggnnn nngagccggc gagacacgcc    60
ctta                                                                 64

<210> SEQ ID NO 73
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 73
```
gcgcggccaa cggggccctg gctacgatcc gacttggnnn nntatgattt ctaggttctc    60
aaag    64

<210> SEQ ID NO 74
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 74
ccggcccgaa cgggcgcctg gctacgatcc gacttggnnn nngctttggc tgtggtcaac    60
ttac    64

<210> SEQ ID NO 75
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 75
ccgggccgat ggccccgctg gctacgatcc gacttggnnn nntcatggcc tgaggcaggc    60
actc    64

<210> SEQ ID NO 76
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 76
cccggcccaa ggccgccgtg gctacgatcc gacttggnnn nngatagcag caaggggctc    60
ttac    64

<210> SEQ ID NO 77
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 77
cgggccggaa ggcgcggctg gctacgatcc gacttggnnn nntcgggcca ttttggagaa    60
ttcg    64

<210> SEQ ID NO 78
<211> LENGTH: 64

<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 78
ccccgggcat cgcggcgctg gctacgatcc gacttggnnn nnaagcacag actgcaattt    60
gtac    64

<210> SEQ ID NO 79
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 79
ccgggcgcta ccccgcggtg gctacgatcc gacttggnnn nngatgttgc ttctcttaat    60
tcct    64

<210> SEQ ID NO 80
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 80
ccgggcgcaa cgccggcctg gctacgatcc gacttggnnn nnacacagca aagcagaaac    60
tcac    64

<210> SEQ ID NO 81
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 81
gccggcccaa cgcggggctg gctacgatcc gacttggnnn nngtcaaggc gcctgtgggg    60
tctg    64

<210> SEQ ID NO 82
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)

<223> OTHER INFORMATION: n is a, c, g, or t

<400> SEQUENCE: 82
cgcgcgcgaa cggcgcgctg gctacgatcc gacttggnnn nntgtttcca gacaagccac    60
tcac    64

<210> SEQ ID NO 83
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 83
ggcgcgggta cccccccgtg gctacgatcc gacttggnnn nnttcctcca tctcatagct    60
gtcg    64

<210> SEQ ID NO 84
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 84
ggggcgccaa ccggcgcgtg gctacgatcc gacttggnnn nncgcacacc ggcgggcttc    60
ctac    64

<210> SEQ ID NO 85
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 85
cccggccgta gcgcgcgctg gctacgatcc gacttggnnn nngtggcagc agtcactggg    60
ggac    64

<210> SEQ ID NO 86
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 86
ggccgcccta cccccccgtg gctacgatcc gacttggnnn nnggctgctg gaggggcatc    60
ttac    64

<210> SEQ ID NO 87
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 87
cggcgcccaa gcgcccgctg gctacgatcc gacttggnnn nntcagtttc cttcaagatc      60
ctca                                                                  64

<210> SEQ ID NO 88
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 88
ggcgccccat ggccccgtg gctacgatcc gacttggnnn nnaggcctgt gccagggacc       60
ttac                                                                  64

<210> SEQ ID NO 89
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 89
cgccgggcaa gccgcggctg gctacgatcc gacttggnnn nngaagtgtt taatattcgt      60
agca                                                                  64

<210> SEQ ID NO 90
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 90
cccgcgcgat gcgcgccgtg gctacgatcc gacttggnnn nnagcaactg aacctgtgac      60
tcac                                                                  64

<210> SEQ ID NO 91
<211> LENGTH: 64
<212> TYPE: DNA
<213> ORGANISM: Artificial
<220> FEATURE:

<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 91
cccccgggaa cgggggggctg gctacgatcc gacttggnnn nnggctccgg gccccagcag    60
ccct                                                                  64

<210> SEQ ID NO 92
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 92
cgccgcggaa gcgcgcggtg gctacgatcc gacttggnnn nncctgcctc ggctgacatt    60
ccgg                                                                  64

<210> SEQ ID NO 93
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 93
cgcgcgcgaa gccggggtg gctacgatcc gacttggnnn nngattaaag aaataacctc    60
ctac                                                                  64

<210> SEQ ID NO 94
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 94
cccggcggaa cccgccgctg gctacgatcc gacttggnnn nnatgctctc cacgttgcac    60
aggg                                                                  64

<210> SEQ ID NO 95
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 95

```
ccgccccgta gcgcgccgtg gctacgatcc gacttggnnn nngttgctga gaaagtcact    60
gctg                                                                 64

<210> SEQ ID NO 96
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 96
ggggcgcgat gccggccgtg gctacgatcc gacttggnnn nnatagtgtg tatgcgacac    60
ttac                                                                 64

<210> SEQ ID NO 97
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 97
ggcggccgta ggggcggctg gctacgatcc gacttggnnn nnagagcatg agtgggggc    60 aggt                                                                 64

<210> SEQ ID NO 98
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 98
gccgccccat gggggggcgtg gctacgatcc gacttggnnn nncccctcggg gttcacatcc    60 atct                                                                 64

<210> SEQ ID NO 99
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 99
cccgcgggta gccggcgctg gctacgatcc gacttggnnn nngggcccac agaggaggac    60
tcac                                                                 64

<210> SEQ ID NO 100
```

<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 100
cggccgggaa ggcggcggtg gctacgatcc gacttggnnn nncaccacca gcagcaagag    60
gagg    64

<210> SEQ ID NO 101
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 101
ggcggccgta cggcgccgtg gctacgatcc gacttggnnn nncgatgtgg cgccttcgca    60
tgaa    64

<210> SEQ ID NO 102
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 102
gcgcgccgta gcgccggctg gctacgatcc gacttggnnn nncccaccca ggactggcac    60
tcac    64

<210> SEQ ID NO 103
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 103
gggcggcgta gccgcgcgtg gctacgatcc gacttggnnn nnctggcagg gattccgtca    60
tatg    64

<210> SEQ ID NO 104
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature

```
<222> LOCATION: (38)..(42)
<223> OTHER INFORMATION: n is a, c, g, or t

<400> SEQUENCE: 104
ggcggccgat gccgcgcgtg gctacgatcc gacttggnnn nnagggaggc gttctccttt    60
ctcc                                                                 64

<210> SEQ ID NO 105
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 105
gcggggccat ggccggcgtg gctacgatcc gacttggnnn nngacagacc caccagtcac    60
tcac                                                                 64

<210> SEQ ID NO 106
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 106
ggccccggta ggcccggctg gctacgatcc gacttggnnn nnggaggctg agaaaatgat    60
cttc                                                                 64

<210> SEQ ID NO 107
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 107
gcgcggggat gggggcgtg gctacgatcc gacttggnnn nnaaattccc aaggaccacc     60
tcac                                                                 64

<210> SEQ ID NO 108
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 108
ggccggccaa cccgggcgtg gctacgatcc gacttggnnn nntaggaaaa tcaaagtcac    60
``` caac                                                                64

<210> SEQ ID NO 109
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 109
cgccgcccaa cgggcccgtg gctacgatcc gacttggnnn nncaccagta cgttcctggc    60
tgcc                                                                64

<210> SEQ ID NO 110
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 110
gcgggcggaa ccgcgccctg gctacgatcc gacttggnnn nnccagccca aaatctgtga    60
tctt                                                                64

<210> SEQ ID NO 111
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 111
gcgcgcggaa cgggcccgtg gctacgatcc gacttggnnn nntgacctaa agccacctcc    60
ttac                                                                64

<210> SEQ ID NO 112
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 112
ccggcgccta gcgcgggctg gctacgatcc gacttggnnn nncgggcagg tcttgacgca    60
gtgg                                                                64

<210> SEQ ID NO 113
<211> LENGTH: 64
<212> TYPE: DNA
<213> ORGANISM: Artificial

<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 113
gggcgggcat cggcgcgctg gctacgatcc gacttggnnn nnacttccag accagggtgt    60
tgtt    64

<210> SEQ ID NO 114
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 114
gccggggcaa ggggccgctg gctacgatcc gacttggnnn nnttctcctt cactttccac    60
tcac    64

<210> SEQ ID NO 115
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 115
cccgggcgat gccgcggctg gctacgatcc gacttggnnn nnttcatcca tcagggcacg    60
gtag    64

<210> SEQ ID NO 116
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 116
cgggggggaa gcgggcgctg gctacgatcc gacttggnnn nntgaggtac tcgtcggcat    60
ccac    64

<210> SEQ ID NO 117
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 117
gcccggggaa ggcgcgcctg gctacgatcc gacttggnnn nngagagaga cagagatttc    60
atac    64

<210> SEQ ID NO 118
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 118
gggccggcat gcgggggtg gctacgatcc gacttggnnn nngatgatct gcaggttttc     60
caaa    64

<210> SEQ ID NO 119
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 119
ggccggcgat gccggcgctg gctacgatcc gacttggnnn nnctgctaag cataggaat    60 tttc    64

<210> SEQ ID NO 120
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 120
gggcgccgta cgccggggtg gctacgatcc gacttggnnn nnccttggca tcccagcctc    60
tcac    64

<210> SEQ ID NO 121
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 121
gccggcggaa gcgccgggtg gctacgatcc gacttggnnn nngagctgca cggtggaggt    60
gagg    64

-continued

```
<210> SEQ ID NO 122
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 122
cccgcccgta gccgcgcgtg gctacgatcc gacttggnnn nncatagtcc aggaggcagc    60
cgaa                                                                 64

<210> SEQ ID NO 123
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 123
gcgggcccat ccggcggctg gctacgatcc gacttggnnn nncgtatctc ccttccctga    60
ttac                                                                 64

<210> SEQ ID NO 124
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 124
gcggccccaa gggccgggtg gctacgatcc gacttggnnn nntctccatc acttatctcc    60
ttga                                                                 64

<210> SEQ ID NO 125
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 125
ggcgggggaa cggccccctg gctacgatcc gacttggnnn nnatttgcat agcacaaatt    60
tttg                                                                 64

<210> SEQ ID NO 126
<211> LENGTH: 64
<212> TYPE: DNA
<213> ORGANISM: Artificial
<220> FEATURE:
<223> OTHER INFORMATION: Primer
<220> FEATURE:
```

<221> NAME/KEY: misc_feature
<222> LOCATION: (38)..(42)
<223> OTHER INFORMATION: n is a, c, g, or t

<400> SEQUENCE: 126
ggcgggccta cgccccgctg gctacgatcc gacttggnnn nntaaacaga aagcggtgac    60
ttac                                                                 64

<210> SEQ ID NO 127
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 127
cgcgccccaa cccgcggctg gctacgatcc gacttggnnn ncggggttc agaggctgat     60 tgtg                                                                 64

<210> SEQ ID NO 128
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 128
ccgggccgta ggggggggtg gctacgatcc gacttggnnn nnactcgggg ttgcccactg    60
cagt                                                                 64

<210> SEQ ID NO 129
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 129
gggcggggat ggccccgtg gctacgatcc gacttggnnn nncccagtgg gcagggctgt     60
cgaa                                                                 64

<210> SEQ ID NO 130
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 130
cgcccccgaa ggccccggtg gctacgatcc gacttggnnn nngaaagaag tcctgctggt    60
agtc                                                               64

<210> SEQ ID NO 131
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 131
cggcgccgaa cgcggcgctg gctacgatcc gacttggnnn nnggtattct gcattttcag   60
ctgt                                                               64

<210> SEQ ID NO 132
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(42)
<223> OTHER INFORMATION: n is a, c, g, or t

<400> SEQUENCE: 132
cccccgcgta ccccgcggtg gctacgatcc gacttggnnn nngggctcat actatcctcc   60
gtgg                                                               64

<210> SEQ ID NO 133
<211> LENGTH: 61
<212> TYPE: DNA
<213> ORGANISM: Artificial
<220> FEATURE:
<223> OTHER INFORMATION: Forward universal primer

<400> SEQUENCE: 133
tgtgagccaa ggagttgaag tggcgcattg tcttcctaag accgcttggc ctccgacttc   60
c                                                                  61

<210> SEQ ID NO 134
<211> LENGTH: 27
<212> TYPE: DNA
<213> ORGANISM: Artificial
<220> FEATURE:
<223> OTHER INFORMATION: Reverse universal primer
<220> FEATURE:
<221> NAME/KEY: misc_feature
<222> LOCATION: (1)..(1)
<223> OTHER INFORMATION: phosphorylation modification

<400> SEQUENCE: 134
gaacgacatg gctacgatcc gacttgg                                      27

<210> SEQ ID NO 135
<211> LENGTH: 17
<212> TYPE: DNA
<213> ORGANISM: Artificial
<220> FEATURE:
<223> OTHER INFORMATION: first universal sequence

<400> SEQUENCE: 135

```
cttggcctcc gacttcc                                                  17

<210> SEQ ID NO 136
<211> LENGTH: 19
<212> TYPE: DNA
<213> ORGANISM: Artificial
<220> FEATURE:
<223> OTHER INFORMATION: second universal sequence

<400> SEQUENCE: 136
tggctacgat ccgacttgg                                                19
```

PCR PRIMER PAIR AND APPLICATION THEREOF

CROSS REFERENCE TO RELATED APPLICATIONS

This application is a US national phase application based upon PCT Application No. PCT/CN2017/089199 filed on Jun. 20, 2017, the entire content of which is incorporated herein by reference.

FIELD

The present disclosure relates to the field of biotechnology, in particular to PCR primer pair and application thereof.

BACKGROUND

The development of next-generation sequencing technology has created a new situation for the research of modern genomics, however, the cost of whole-genome sequencing and complex analysis bring great difficulty to researchers. Despite the increasing throughput and decreasing cost of the next-generation sequencing (NGS), the NGS is still not a viable option for most genetic laboratories, especially for studies of complex diseases which require at least hundreds of samples to reach sufficient statistical capacity, however, whole-genome sequencing of such numerous samples is still challenging in consideration of cost and data analysis.

The discovery of target sequence capture technology has alleviated the above problems. Among them, target region-targeted enrichment sequencing technology (i.e. Target region sequencing) is a technology which enriches target genes of interest and combines the next-generation sequencing technology so as to obtain base information of target regions, thereby realizing the purpose of disease detection. Compared to whole genome sequencing, targeted enrichment sequencing technology can reduce the cost of sequencing, simplify the process of information analysis, increase the sequencing depth of target region, and improve the sensitivity and accuracy of detection results.

Currently, one of the most important technologies for enriching a target region on the market is the multiplex PCR-based enrichment technology. Despite short experimental time, complex primer design is required at the early stage, and lots of tedious work for primer optimization is required at the later stage. In addition, there is a strict requirement on the quantity and integrity of template, and cell free DNA, highly degradable DNA, paraffin-embedded and formaldehyde-fixed medical samples and the like cannot be enriched by this method.

Therefore, there is an urgent need for a PCR-targeted enrichment technology with strong specificity, simple experimental operation and no need for primer optimization.

SUMMARY

The present disclosure aims to solve at least one of the technical problems existing in the prior art. For the purpose, an object of the present disclosure is to propose a PCR primer design strategy, corresponding PCR primer pairs and PCR targeted enrichment techniques based on the PCR primer pair, in which the PCR primer design strategy can effectively reduce GC bias during PCR amplification, improve amplification specificity, do not need optimization design and facilitate enrichment of amplification products.

First, it should be noted that the present disclosure has been completed based on the following findings of present inventors.

There are various websites and software available online for free services of online primer design, such as NetPrimer. Lots of different stand-alone primer design software has been commonly used, with their own advantages. For example, Rightprimer™ (Bio2Disk), which has excellent proofreading function, can find out primers having highly strong specificity to sequences to be amplified in a short time by searching Genebank and aligning possible primers with background DNAs. Oligo™ (Molecular Biology Insights, Inc.) is suitable for designing primers for Multiplex PCR and Consensus PCR, and can provide suitable PCR conditions. PrimerPremier (or Premierbiosoft) can design primers according to protein sequences in the case of unknown nucleic acid sequences, which can be especially useful in cloning new genes when only part of protein sequences are known. PrimerDesigner210 (Scientific and Educational Software) is widely used due to its small size and complete functionality.

However, good primers designed by conventional primer design software do not definitely produce good results in practical working, especially for templates containing high GC regions and sequences similar to other target regions, thus ultimately resulting in poor specificity for the product amplified in the presence of the primers, as well as poor PCR amplification efficiency. In addition, the primers with optimization for these regions usually cannot get satisfactory results. The present inventors after research have found that current PCR primers are required to be designed according to strict primer design conditions. PCR specificity and amplification efficiency greatly depend on the quality of primer designed, thus the primers generally cannot get good results in some repeat regions, high GC regions or regions with advanced structures, thereby plenty of energy and resources will cost for primer design and optimization. Thus, the present inventors have conducted a series of design and experimental explorations to solve the problems. Further, it is surprisingly discovered by the present inventors that such problems can be effectively addressed by addition of a pair of complementary sequences at the 5' ends of a conventional primer pair thus forming a primer pair with a stable primer-dimer structure which is reversely complementary at the 5' end and overhanging at the 3' end. Moreover, the present inventors have also discovered that a molecular tag and a universal sequence used for subsequent second amplification of the first PCR amplification product can be introduced between the specific sequence and the random sequence respectively, therefore the molecular tag can be used to label original template and remove PCR errors, sequencing errors and amplification bias in subsequent information analysis process, thus improving sensitivity of mutation detection; and the universal sequence, which may be a portion of sequence of a sequencing adaptor for different sequencing platforms, can be used for subsequent amplification and introduction of sequencing primer.

Further, the present inventors have developed a PCR-based targeted enrichment technology, that is, circular multiplex PCR technology (i.e. CMP). Specifically, the circular multiplex PCR includes capturing a target region firstly and subsequently adding sequence of a sequencing primer into two ends of the target region respectively through one-step universal amplification, thus realizing capture of target region and preparation of library via a two-step PCR reaction, reducing steps of library preparation. In the first step of the PCR reaction, the target region is captured to form a ring, with non-specific products removed by enzymatic digestion; and in the second step of the PCR reaction, the captured target region is added with a specific sequencing primer (such as, sequencing primer for platforms BGISEQ-500, proton or Illumina) at two ends respectively, and resulting products are further enriched.

Thus, in a first aspect, the present disclosure in embodiments provides a PCR primer pair. In embodiments of the present disclosure, the PCR primer pair comprises a first primer and a second primer, wherein the first primer comprises a first specific sequence, a first random sequence and a first universal sequence, and the second primer comprises a second specific sequence, a second random sequence and a second universal sequence, wherein the first specific sequence is located at the 3' end of the first primer, the first random sequence is located at the 5' end of the first primer, and the first universal sequence is located between the first specific sequence and the first random sequence, the second specific sequence is located at the 3' end of the second primer, the second random sequence is located at the 5' end of the second primer, and the second universal sequence is located between the second specific sequence and the second random sequence, wherein the first specific sequence and the second specific sequence are respectively an upstream primer and a downstream primer for a target sequence, and the first random sequence and the second random sequence are reversely complementary. The present inventors have surprisingly found that the PCR primer pair of the present disclosure can effectively reduce the GC bias during PCR amplification, thus increasing amplification specificity. Specifically, use of conventional primers will result in GC bias to some extent during PCR enrichment of the next-generation sequencing library, but the PCR primer pair of the present disclosure (sometimes referred to as "Padlock Primer") is capable of effectively reducing the GC bias during library PCR enrichment. Moreover, the first PCR amplification product, because carrying the universal sequence, can be subjected to second PCR amplification conveniently, thus realizing the enrichment of target region sequence.

In a second aspect, the present disclosure in embodiments also provides a PCR amplification kit. In embodiments of the present disclosure, the kit comprises the PCR primer pair as described above. In embodiments of the present disclosure, using the kit comprising the PCR primer pair of the present disclosure for PCR amplification, can bring low GC bias, high amplification specificity and excellent amplification effect during amplification, compared to conventional primers. Moreover, the first PCR amplification product, because carrying the universal sequence, can be subjected to second PCR amplification conveniently, thus realizing the enrichment of target region sequence.

In a third aspect, the present disclosure in embodiments provides a method for PCR amplification. In embodiments of the present disclosure, the method performs the PCR amplification by using the PCR primer pair or the PCR amplification kit as described above. Thus, PCR amplification of template can be effectively achieved through this method. Further, the method is capable of increasing specificity of PCR amplification, effectively reducing generation of non-specific products, and improving amplification efficiency. Moreover, the first PCR amplification product, because carrying the universal sequence, can be subjected to second PCR amplification conveniently, thus realizing the enrichment of target region sequence.

In a fourth aspect, the present disclosure in embodiments provides a method for enriching a target region sequence of a DNA sample to be tested. In embodiments of the present disclosure, the method comprises the steps of:

(1) subjecting the DNA sample to be tested to a first PCR amplification in the presence of a PCR primer pair targeting the target region sequence according to the method for PCR amplification as described above, so as to obtain a first PCR amplification product comprising a loop-like substance, wherein the 5' end and the 3' end of the loop-like substance are not connected, at least one of the first primer and the second primer of the PCR primer pair is subjected to phosphorylation modification at the 5' end, the $1$-$5^{th}$ bases from each of the 5' end and the 3' end of the first primer are respectively subjected to thio-modification, the $1$-$5^{th}$ bases from each of the 5' end and the 3' end of the second primer are respectively subjected to thio-modification, and (2) subjecting the first PCR amplification product comprising the loop-like substance to a second PCR amplification in the presence of a forward universal primer and a reverse universal primer, so as to obtain a second PCR amplification product, the second PCR amplification product constituting the target region sequence of the DNA sample to be tested, wherein a portion of base sequence from the 3' end of the forward universal primer is same as the first universal sequence in the PCR primer pair, and a portion of base sequence from the 3' end of the reverse universal primer is same as the second universal sequence in the PCR primer pair.

In embodiments of the present disclosure, use of the method can effectively realize the enrichment of target region sequence of the DNA sample to be tested. Further, the method is of good repeatability, high enrichment efficiency, and good specificity for the enriched sequence.

In embodiments of the present disclosure, the PCR primer pair of the present disclosure and use thereof have at least one of the following advantages:

1. The design strategy of the PCR primer pair of the present disclosure simplifies the primer design flow and optimizes the experimental steps. Each primer of the primer pair consists of a specific sequence at the 3' end and a random sequence (i.e. a complementary sequence) at the 5' end, thus the forward primer and the reverse primer form a stable dimer structure through complementary sequences, which does not need to meet strict conditions as conventional primers, thus greatly simplifying the design process. During conventional primer design, complementation of the 5' end and the 5' end of primers, generation of palindrome structure via primer itself and the like are necessarily to be avoided so as to ensure that no dimer structure is formed between primers and no self-extension of primers occurs for PCR. However, for design of the PCR primer pair of the present disclosure, such problems are not necessary to be considered, because the padlock primer is of a stable dimer structure, of which the 5' ends are complementary with each other and the 3' ends can complement with specific sequences of template and extend normally; in contrast, for a conventional primer pair, if its 5' ends are complementary with each other, its 3' ends will have no enough sequence to complement with specific sequences of template. Moreover, the complementary sequences at the 5' end formed between two primers of the padlock primer pair of the present disclosure display potential energy which is greatly stronger than that of self-palindrome structure, thus the dimer structure at the 5' end is preferably formed even the 5' end and the 3' end have sequences complementary with each other. Moreover, a molecular tag and a universal sequence used for subsequent second amplification of the first PCR amplification product are respectively introduced between the specific sequence and the random sequence (refer to FIG. 2), so that the molecular tag can be used to label original template and remove PCR errors, sequencing errors and amplification bias in subsequent information analysis process, thus improving sensitivity of mutation detection; and the universal sequence, which may be a portion of sequence of a sequencing adaptor for different sequencing platforms, can be used for subsequent amplification and introduction of sequencing primer.

2. The PCR amplification method of the present disclosure can increase specificity of PCR amplification, thus effectively reducing generation of non-specific products. Starting from the second PCR cycle, bases at the 5' end of the primer (i.e. the random sequence) can reversely complement with bases at the 5' end of the newly-generated template, and the specific sequence at the 3' end of the primer can reversely complement with bases at the 3' end of the newly-generated template, that is, two recognition sites for binding between primer and template (refer to FIG. 3), thus significantly increasing binding ability between primer and template, and amplification specificity. Further, amplification efficiency is also effectively improved due to the increased binding ability.

3. Using the PCR primer pair of the present disclosure for PCR amplification can effectively reduce GC bias of different templates in amplification of sequencing libraries (especially, the next-generation sequencing library), because effective PCR amplification is only carried out after denaturation of template and binding of primer to template. The GC bias is generated because template containing some high GC regions would have renatured rapidly before the primer binds to the template during PCR amplification, thus these high GC regions cannot be efficiently amplified. For the padlock primer of the present disclosure, two recognition sites for binding primer to template are presented, which can greatly improve the binding ability between primer and template, thereby the primer pair can be effectively paired with template containing high GC regions, thus reducing the GC bias.

4. The products obtained by the PCR amplification method of the present disclosure are loop-like substances with a nick (that is, the 5' end and the 3' end of the loop-like substance are not connected), thus for experiments where the products have to be cyclized, the cyclization can be realized by addition of a ligase, without complex denaturation, quenching and the like steps, thereby effectively simplifying the experimental process.

5. The first PCR amplification product obtained in the presence of the PCR primer pair of the present disclosure can be subjected to second PCR amplification because carrying the universal sequence, so as to realize the enrichment of target region sequence and the introduction of sequencing primer, thus the target region sequence containing sequence of a sequencing adaptor can be enriched conveniently, that is, obtaining a target sequencing library.

Additional aspects and advantages of the present disclosure will be given in the following description partly, part of which will become apparent from the following description or be acknowledged through the practice of the present disclosure.

BRIEF DESCRIPTION OF THE DRAWINGS

The above and/or additional aspects and advantages of the present disclosure will become apparent and easily understood from the description of the embodiments in combination with the following drawings, in which.

DETAILED DESCRIPTION

Figure 1:
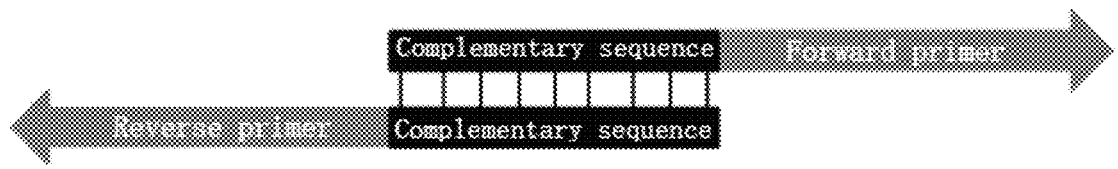
FIG. 1 is a schematic diagram showing the structure of a PCR primer pair (i.e. a padlock primer) of the present disclosure according to an embodiment of the present disclosure.

Embodiments of the present disclosure are described in detail below, examples of which are illustrated in the accompanying drawings. The embodiments described below with reference to the accompanying drawings are intended to be illustrative and for explanation of the present disclosure, which cannot be construed as limiting.

It should be noted, the terms "first" and "second" are used for purposes of description and are not intended to indicate or imply relative importance or significance or impliedly indicate quantity of the technical feature referred to. Thus, the feature defined with "first" and "second" may comprise one or more this feature either explicitly or implicitly. Further, in the description of the present disclosure, "a plurality of" means two or more than two, unless specified otherwise.

PCR Primer Pair

In a first aspect, the present disclosure in embodiments provides a PCR primer pair. According to embodiments of the present disclosure, the PCR primer pair comprises a first primer and a second primer, in which the first primer comprises a first specific sequence, a first random sequence and a first universal sequence, and the second primer comprises a second specific sequence, a second random sequence and a second universal sequence, in which the first specific sequence is located at the 3' end of the first primer, the first random sequence is located at the 5' end of the first primer, and the first universal sequence is located between the first specific sequence and the first random sequence; the second specific sequence is located at the 3' end of the second primer, the second random sequence is located at the 5' end of the second primer, and the second universal sequence is located between the second specific sequence and the second random sequence, in which the first specific sequence and the second specific sequence are respectively an upstream primer and a downstream primer for a target sequence, and the first random sequence and the second random sequence are reversely complementary. The present inventors have surprisingly found that the PCR primer pair of the present disclosure can effectively reduce the GC bias during PCR amplification, thus increasing amplification specificity. Specifically, use of conventional primers will result in GC bias to some extent during PCR enrichment of the next-generation sequencing library, but the PCR primer pair of the present disclosure (sometimes referred to as "Padlock Primer") is capable of effectively reducing the GC bias during library PCR enrichment. Moreover, the first PCR amplification product, because carrying the universal sequence, can be subjected to second PCR amplification conveniently, thus realizing the enrichment of target region sequence.

It should be noted that the "first random sequence" and the "second random sequence" of the present disclosure may be unfixed or fixed sequences as long as they are reversely complementary to each other.

The "universal sequence" described herein is a conventional term in the art, which refers to a sequence used to pair with a specific sequence in primer for subsequent PCR amplification, including sequence of an adaptor for a sequencing platform (i.e. a sequencing adaptor). The PCR amplification product obtained in the presence of the PCR primer pair of the present disclosure contains the "first universal sequence" and the "second universal sequence", thus use of a primer pair comprising sequences respectively pairing with the "first universal sequence" and the "second universal sequence" can realize the subsequent PCR enrichment (may referred to as "second PCR amplification" herein). For example, the first universal sequence and the second universal sequence can be respectively designed to be a portion of sequence of a sequencing adaptor. Base sequence from the 3' end of the forward and reverse primers for second PCR amplification are designed to be same as the first universal sequence and the second universal sequence respectively, that is, a portion of sequence of a sequencing adaptor; and the remaining sequence of the forward and reverse primers is designed to be same as the other portion of sequence of the sequencing adaptor respectively. Thus, the second PCR amplification can be effectively performed, thereby realizing the enrichment of PCR amplification products obtained in the presence of the PCR primer pair of the present disclosure, and a complete sequence of sequencing adaptor can be introduced conveniently, such that the second PCR amplification product has sequence of the sequencing adaptor, which can be directly used in the corresponding sequencing platform.

According to some specific examples of the present disclosure, the first universal sequence and the second universal sequence each have a length of 15-20 bp.

According to embodiments of the present disclosure, the first specific sequence and the second specific sequence each have a TM value of 55-65° C., and the first primer and the second primer each have a TM value of 65-75° C. Thus, the PCR reaction is subjected to a first round of linear amplification under a low annealing temperature of 55-65° C., followed by a second round of circular amplification under a high annealing temperature of 65-72° C. in subsequent cycles. During the circular amplification, the specific sequence of primer cannot bind to the specific site of template directly because the specific sequence has a TM value of 55-65° C. which is lower than the high annealing temperature of circular amplification. Such a circular amplification can be effectively performed only when the 5' end and the 3' end of the padlock primer bind to the 5' end and the specific site of template respectively, i.e. performing the circular amplification through two recognition-site binding.

The PCR primer pair of the present disclosure is suitable for PCR amplification and library construction for any form of DNA sample to be tested. It should be noted that the "DNA sample to be tested" described in the present disclosure is somewhat different from the conventional understanding which does not include treated DNA. However, in the present disclosure, the "DNA sample to be tested" may include both treated DNA and untreated DNA. Generally, during construction of sequencing library, the genomic DNA of sample will be fragmented and added with adaptor for sequencing, thus obtaining DNA fragments carrying sequencing adaptor corresponding to a sequencing platform, which will be subjected to subsequent amplification and other steps for obtaining sequencing products. Such a DNA fragment carrying sequencing adaptor corresponding to a sequencing platform is called as the "treated DNA". Correspondingly, DNA fragments which are not treated according to the method as described above are called the "untreated DNA". If the PCR primer pair of the present disclosure is for untreated DNA, specific target fragments can be amplified; but if the PCR primer pair of the present disclosure is for treated DNA, whole genomic DNA fragments can be amplified.

According to some embodiments of the present disclosure, when the DNA sample to be tested is the treated DNAs which are DNA fragments containing a sequencing adaptor, the first specific sequence and the second specific sequence have to specifically recognize a target sequence carrying the sequencing adaptor accordingly, that is, the target sequence actually consists of a sequencing adaptor and a target region sequence. When the DNA sample to be tested is DNA fragments which do not carry a sequencing adaptor, i.e. template for PCR reaction, the first specific sequence and the second specific sequence have to specifically recognize the target sequence accordingly. Meanwhile, if a sequencing library is required to be constructed, adaptor sequence for sequencing can be inserted into the random sequence or between the specific sequence and the random sequence for the first primer and the second primer respectively, so that PCR amplification products can be ligated with adaptors, thus can be effectively used in sequencing platforms.

According to embodiments of the present disclosure, the first random sequence and the second random sequence each have a length of 15-45 bp, and the first specific sequence and the second specific sequence each have a length of 15-30 bp.

According to embodiments of the present disclosure, the 1-5$^{th}$ bases from each of the 5' end and the 3' end of the first primer are respectively subjected to thio-modification, and the 1-5$^{th}$ bases from each of the 5' end and the 3' end of the second primer are respectively subjected to thio-modification, so as to effectively prevent from cleavage by exonuclease.

According to some embodiments of the present disclosure, the type of thio-modification is not particularly limited as long as the first primer and the second primer can be prevented from cleavage by exonuclease, such as cleavage by 5-3' exonuclease or 3-5' exonuclease. According to some specific examples of the present disclosure, the thio-modification is any one selected from phosphorothioate modification, methyl-sulfate modification and peptide nucleic acid modification.

According to embodiments of the present disclosure, at least one of the first primer and the second primer is subjected to phosphorylation modification at the 5' end. Thus, a loop-like substance with a nick which is obtained after two rounds of amplification (that is, the 5' end and the 3' end of the loop-like substance are not connected) can be ligated by a ligase so as to form complete circular DNAs.

According to embodiments of the present disclosure, the first primer further comprises a first molecular tag, and the first molecular tag is located between the first universal sequence and the first specific sequence; and the second primer further comprises a second molecular tag, and the second molecular tag is located between the second universal sequence and the second specific sequence. Thus, a plurality of samples can be subjected to PCR amplification simultaneously, and the plurality of samples each can be distinguished based on the sequences of molecular tags. According to embodiments of the present disclosure, the first molecular tag and the second molecular tag of the present disclosure are both used to label the original template, thus sequencing errors and bias and errors in PCR can be corrected. Further, the first molecular tag and the second molecular tag of the present disclosure each consist of a randomly-generated base sequence, therefore the greater the number of base sequence used, more templates can be labeled. Furthermore, when each primer of a PCR primer pair is disposed with two molecular tags composed of randomly-generated base sequences, the PCR primer pair exhibits significantly increased ability of labeling template.

Therefore, according to some specific examples of the present disclosure, the first molecular tag and the second molecular tag have different sequences. According to other embodiments of the present disclosure, the first molecular tag and the second molecular tag each have a sequence in a length of 5-10 bp. Thus, the PCR primer pair, in which its forward and reverse primers each are introduced with a molecular tag in a sequence length of 5-10 bp, can label up to $4^{10-20}$ types of base sequences. As described above, for each of the forward and reverse primers, the 5-10 bp of molecular tag is randomly generated, thus resulting in $4^{10-20}$ types of base sequence combinations, thereby being capable of labeling up to $4^{10-20}$ types of templates. Thus, sequencing errors and bias and errors in PCR can be corrected by tracing base information of the original template via the molecular tag.

Figure 2:
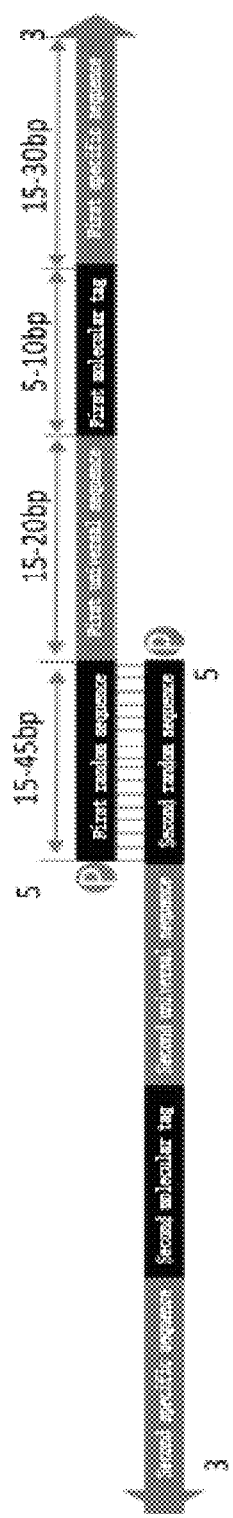
FIG. 2 is a schematic diagram showing the structure of a PCR primer pair (i.e. a padlock primer) of the present disclosure according to another embodiment of the present disclosure.

In addition, it should be noted, referring to FIG. 1 and FIG. 2 which show the schematic structure of the PCR primer pair of the present disclosure, the design strategy of the PCR primer pair of the present disclosure includes addition of a pair of complementary sequences at the 5'-ends of a conventional primer pair (including a forward primer and a reverse primer), thus forming a PCR primer pair (i.e. Padlock Primer, PP) which is reversely complementary at the 5' end and overhanging at the 3' end, in which two primers of the padlock primer pair form a stable primer-dimer structure, and the complementary sequences may be unfixed or fixed sequences. The first primer and the second primer of the PCR primer pair each have a length of 30-70 bp, and have a high TM value, generally of 65-75° C. The complementary sequences (i.e. the first random sequence and the second random sequence, being unfixed or fixed sequences) at the 5'-end of the padlock primer pair each have a length of 15-45 bp. The first specific sequence and the second specific sequence at the 3'-ends of the padlock primer pair, which are complementary to target sequences of a template, each have a length of 15-30 bp, and have a low TM value, generally of 55-65° C. Moreover, a molecular tag and a universal sequence used for subsequent second amplification of the first PCR amplification product are respectively introduced between the specific sequence and the random sequence (refer to FIG. 2), so that the molecular tag can be used to label original template and remove PCR errors, sequencing errors and amplification bias in subsequent information analysis process, thus improving sensitivity of mutation detection; and the universal sequence, which may be a portion of sequence of a sequencing adaptor for different sequencing platforms, can be used for subsequent amplification and introduction of sequencing primer.

Figure 3:
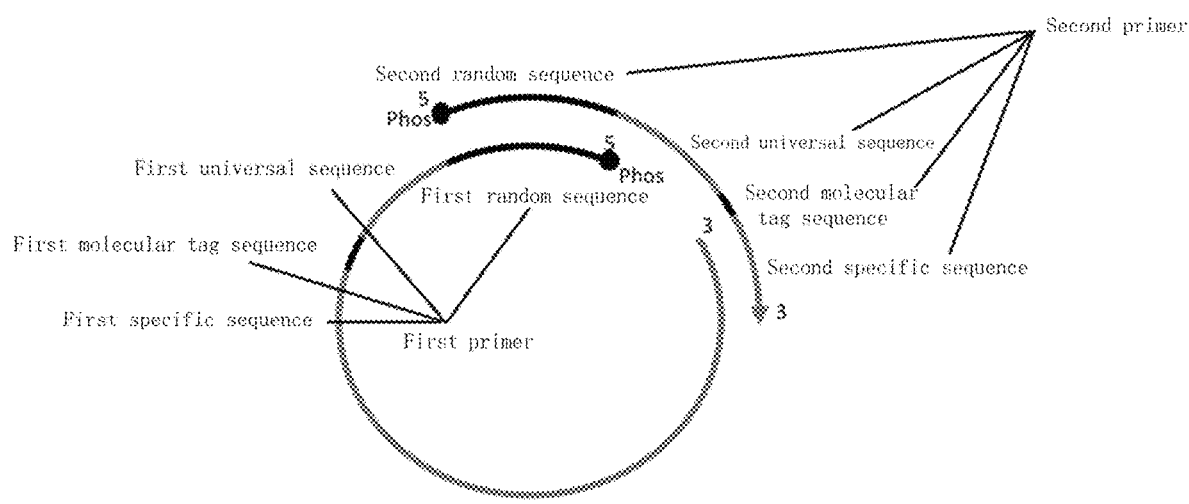
FIG. 3 is a schematic diagram showing binding between primer and newly-generated strand during circular amplification according to an embodiment of the present disclosure.

Further, for the application of the PCR primer pair of the present disclosure, the PCR primer pair of the present disclosure is subjected to two different amplification processes (i.e. two rounds of amplification) to complete the PCR amplification, referring to FIG. 3, in the first round of amplification, the annealing temperature is 55-65° C. and the cycle number is 1; and in the second round of amplification, the annealing temperature is 65-72° C. and the cycle number is 1. During the first round of amplification, only the specific sequence at the 3' end of the PCR primer pair can bind to template, thus the annealing temperature in this round is low. During the second round of amplification, the newly-generated template (i.e. the product of the first round of amplification) is firstly paired with the complementary sequence at the 5' end of the PCR primer pair (i.e. the first random sequence or the second random sequence), followed by pairing with the specific sequence at the 3' end (i.e. the first specific sequence or the second specific sequence), that is, two recognition sites for binding between primer and template, which greatly improved the annealing temperature of primer, resulting in a high annealing temperature.

Further, it should be noted, in the second round of amplification, the circular amplification can be effectively performed only when the 5' end and the 3' end of the primer bind to the newly-generated template simultaneously, thus both specificity of PCR amplification and binding between primer and template are greatly improved via two recognition sites, with improved PCR amplification efficiency. Therefore, using the PCR primer pair of the present disclosure for PCR amplification, is capable of significantly increasing the specificity of PCR amplification, effectively reducing the generation of non-specific products, and reducing the GC bias during amplification, compared to conventional PCR primers. Thus, use of such a primer pair in sequencing, especially in the next-generation sequencing library, can effectively reduce the genome-wide GC bias in library enrichment and amplification.

Further, the first PCR amplification product can be subjected to subsequent second PCR amplification because carrying the universal sequence, so as to realize the enrichment of target region sequence and the introduction of sequencing primer, thus the target region sequence containing sequence of a sequencing adaptor can be enriched conveniently, that is, obtaining a target sequencing library.

In addition, according to embodiments of the present disclosure, the products obtained by PCR amplification in the presence of the PCR primer pair of the present disclosure can be directly cyclized by a ligation reaction, thus obtaining circular DNAs. Specifically, the products can be directly subjected to cyclization in a ligation reaction system, without additional denaturation, quenching and other steps, thus cyclization process is simplified, and the process for preparing a circular DNA library is simplified accordingly.

Application

Further, in a second aspect, the present disclosure in embodiments also provides a PCR amplification kit. According to an embodiment of the present disclosure, the kit comprises the PCR primer pair as described above. According to an embodiment of the present disclosure, using the kit comprising the PCR primer pair of the present disclosure for PCR amplification, can bring low GC bias, high amplification specificity and excellent amplification effect during amplification, compared to conventional primers. Moreover, the first PCR amplification product, because carrying the universal sequence, can be subjected to second PCR amplification conveniently, thus realizing the enrichment of target region sequence.

Further, the present disclosure in embodiments proposes use of the PCR primer pair and the kit comprising the PCR primer pair.

In a third aspect, the present disclosure in embodiments provides a method for PCR amplification. According to embodiments of the present disclosure, the method performs PCR amplification by using the PCR primer pair or the PCR amplification kit as described above. Thus, PCR amplification of template can be effectively achieved by using this method. Further, this method can increase specificity of PCR amplification, effectively reduce generation of non-specific products, and improve amplification efficiency. Moreover, the first PCR amplification product, because carrying the universal sequence, can be subjected to second PCR amplification conveniently, thus realizing the enrichment of target region sequence.

According to an embodiment of the present disclosure, the method comprises two rounds of amplification. In the first round of amplification, the PCR primer pair and a template are subjected to linear amplification under an annealing temperature of 55-65° C., and in the second round of amplification, a product of the linear amplification is subjected to circular amplification under an annealing temperature of 65-72° C. Thus, starting from the second PCR cycle (i.e. circular amplification in the second round), bases at the 5' end of the first primer or the second primer can reversely complement with bases at the 5' end of the newly-generated template, and the specific sequence at the 3' end of the first primer or the second primer can reversely complement with bases at the 3' end of the newly-generated template, that is, two recognition sites for binding between primer and template (refer to FIG. 3), thus increasing specificity of PCR amplification, and effectively decreasing the generation of non-specific products.

According to an embodiment of the present disclosure, the two rounds of amplification are performed as the following amplification reaction procedure:

| | |
|---|---|
| step 1 | preheating for 2 minutes at 98° C. |
| step 2 | denaturing for 10 seconds at 98° C. |
| step 3 | annealing for 5 minutes at 55-65° C. |
| step 4 | amplifying for 30 seconds at 72° C. |
| step 5 | denaturing for 10 seconds at 98° C. |
| step 6 | annealing for 15 minutes at 65-72° C. |
| step 7 | extending for 5 minutes at 72° C. |
| step 8 | holding at 16° C. |

Therefore, the GC bias during PCR amplification is low, the amplification specificity is high and the amplification effect is excellent.

In the fourth aspect, provided in embodiments is a method for enriching a target region sequence of a DNA sample to be tested. According to embodiments, the method comprises the steps of:

(1) subjecting the DNA sample to be tested to a first PCR amplification in the presence of a PCR primer pair targeting the target region sequence according to the method for PCR amplification as described above, so as to obtain a first PCR amplification product comprising a loop-like substance, in which the 5' end and the 3' end of the loop-like substance are not connected, at least one of the first primer and the second primer of the PCR primer pair is subjected to phosphorylation modification at the 5' end, the 1-5$^{th}$ bases from each of the 5' end and the 3' end of the first primer are respectively subjected to thio-modification, the 1-5$^{th}$ bases from each of the 5' end and the 3' end of the second primer are respectively subjected to thio-modification, and (2) subjecting the first PCR amplification product comprising the loop-like substance to a second PCR amplification in the presence of a forward universal primer and a reverse universal primer, so as to obtain a second PCR amplification product, the second PCR amplification product constituting the target region sequence of the DNA sample to be tested, in which a portion of base sequence from the 3' end of the forward universal primer is same as the first universal sequence in the PCR primer pair, and a portion of base sequence from the 3' end of the reverse universal primer is same as the second universal sequence in the PCR primer pair.

According to embodiments of the present disclosure, use of the method can effectively realize the enrichment of target region sequence of the DNA sample to be tested. Further, the method is of good repeatability, high enrichment efficiency, and good specificity for the enriched sequence.

According to embodiments of the present disclosure, prior to the step (2), the method further comprises ligating the first PCR amplification product by a ligase, such that the 5' end and the 3' end of the loop-like substance are ligated to be a ring, thus forming a ligation product; and removing linear DNAs from the ligation product, so as to obtain a circular DNA mixture.

According to embodiments of the present disclosure, the linear DNAs are removed through a linear-chain digestion reaction.

According to specific examples of the present disclosure, the method further comprises the step of purifying the circular DNA mixture.

As described above, the first universal sequence and the second universal sequence can be respectively designed to be a portion of sequence of a sequencing adaptor. Base sequence from the 3' end of the forward and reverse primers for second PCR amplification are designed to be same as the first universal sequence and the second universal sequence respectively, that is, a portion of sequence of a sequencing adaptor; and the remaining sequence of the forward and reverse primers is designed to be same as the other portion of sequence of the sequencing adaptor respectively. Thus, the second PCR amplification can be effectively performed, thereby realizing the enrichment of PCR amplification products obtained in the presence of the PCR primer pair of the present disclosure, and a complete sequence of sequencing adaptor can be introduced conveniently, such that the second PCR amplification product has sequence of the sequencing adaptor, which can be directly used in the corresponding sequencing platform.

According to embodiments of the present disclosure, the first universal sequence and the second universal sequence each are same as a portion of sequence of a sequencing adaptor.

According to some specific examples of the present disclosure, the first universal sequence is of a nucleotide sequence of 5'-CTTGGCCTCCGACTTCC-3' (SEQ ID NO: 135);

the second universal sequence is of a nucleotide sequence of 5'-TGGCTACGATCCGACTTGG-3' (SEQ ID NO: 136); and the forward universal primer is of a nucleotide sequence of (SEQ ID NO: 133)
5'-TGTGAGCCAAGGAGTTGAAGTGGCGCATTGTCTTCCTAAGACC<u>CTTGGCCTCCGACTTCC</u>-3', in which, sequence in the box is same as the first universal sequence and sequence of a sequencing tag is underlined.

The sequence of sequencing tag is used to distinguish sequencing data of different samples to be tested after sequencing, that is, the sequence of sequencing tag can be used to distinguish sample sources of sequencing data. Thus, a plurality of libraries obtained by enriching sequences via the method of the present disclosure can be subjected to sequencing simultaneously.

The reverse universal primer is of a nucleotide sequence of (SEQ ID NO: 134)
5'-phos/GAACGACA<u>TGGCTACGATCCGACTTGG</u>-3', in which sequence in the box is same as the second universal sequence.

According to embodiments of the present disclosure, when a plurality of target region sequences are enriched, the plurality of target region sequences in a DNA sample to be tested are subjected to PCR enrichment via multiplex PCR amplification.

According to some specific examples of the present disclosure, in the step (1), the first PCR amplification is performed in the presence of a set of PCR primer pairs respectively targeting the plurality of target region sequences, in which a first molecular tag and a second molecular tag of each PCR primer pair constituents a tag combination, and the tag combination for each PCR primer pair in the set of PCR primer pairs is unique, so as to label the original DNA template by the tag combination. Thus, the original DNA template can be distinguished effectively based on the sequence of tag combination in the amplified product after sequencing, because each PCR primer pair in the set of PCR primer pairs has a unique tag combination, in which the set of PCR primer pairs refers to all the PCR primer pairs respectively targeting the plurality of target region sequences of a DNA sample to be tested, and the PCR amplification performed in the presence of the set of PCR primer pairs is multiple PCR amplification.

According to embodiments of the present disclosure, the method further comprises: allowing at least one of the forward universal primer and the reverse universal primer to carry a sequencing tag when a plurality of DNA samples to be tested are presented, performing the step (1) and the step (2) for each of the plurality of DNA samples to be tested, and distinguishing the plurality of DNA samples to be tested based on sequences of the sequencing tags after sequencing.

According to other embodiments of the present disclosure, as described above, a first molecular tag and a second molecular tag of each PCR primer pair constituents a tag combination. When a plurality of DNA samples to be tested are presented, each PCR primer pair in the set of PCR primer pairs for one same DNA sample to be tested has a unique tag combination, and each PCR primer pair in the set of PCR primer pairs for different DNA samples to be tested has a unique tag combination as well, thereby distinguishing the original DNA template and sources of DNA samples to be tested based on sequences of tag combinations after sequence enrichment and subsequent sequencing. Thus, for the plurality of DNA sample to be tested, the first PCR amplification product of each DNA sample to be tested can be mixed after performing the step (1) and before any further step, thereby effectively simplifying operation, shortening time and ensuring accuracy of sequencing results as well.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art (for example, referring to J. Sambrook, et al. (translated by Huang PT), *Molecular Cloning: A Laboratory Manual,* 3rd Ed., Science Press) or in accordance with the product instructions. If the manufacturers of reagents or instruments are not specified, the reagents or instruments may be conventional products that are commercially available, for example, from Illumina Company.

Example 1: Detection of Mutation in Exon Region of EGFR Gene of a Sample by Padlock Primer 1.1 Primer Design of Padlock Primer (i.e. PCR Primer Pair of the Present Disclosure, Referred to as "PP Primer" Below)

Primers were designed for the exon region of EGFR gene (covering 28 exons) by the Primer3, with a total of 66 of PCR primer pairs designed, referring to Table 1 and FIG. 2 showing schematic primer structure. For each PCR primer pair targeting amplicon in a length of 80-120 bp, 3' end sequence has a TM value of 55-65° C. and is not specially optimized, and 5' end sequence is a randomly-generated complementary sequence and has a TM value of 65-75° C.

TABLE 1

Primer sequence information

| Sequence No. | Sequence (5'-3', SEQ ID NO:) |
|---|---|
| EGFR1F | GGGGGCGGTTGGGGGCGC*CTTGGCCTCCGACTTCC*NNNNNGTATATTTCTCTTTCACTTCCT(1) |
| EGFR2F | CCGGCCGGATGCGCCGCCCTTGGCCTCCGACTTCCNNNNNGGGCAACTTCTCTGTTTCTTTT(2) |
| EGFR3F | GCGCCGCGATGCGGCCCCCTTGGCCTCCGACTTCCNNNNNATGCATCTATTACTTTTACATT(3) |
| EGFR4F | CGGGGCGGTTGCGGCGCGCTTGGCCTCCGACTTCCNNNNNAATAATCACCCTGTTGTTTGTT(4) |
| EGFR5F | CGGGCCCCATCCGGGGCCCTTGGCCTCCGACTTCCNNNNNACTGCCTCATCTCTCACCATCC(5) |
| EGFR6F | GGGGCGCGTTCGGGGCCCTTGGCCTCCGACTTCCNNNNNCGGAGCGAGCTCTTCGGGGAGC(6) |
| EGFR7F | GGGCCCCGTTGGCCGCGCCTTGGCCTCCGACTTCCNNNNNTCTGAAGTCTTTCATCTGCCTT(7) |
| EGFR8F | GGCGCCCGTTCGGGCCGGCTTGGCCTCCGACTTCCNNNNNCTGAAAACAGGACGGACCTCCA(8) |
| EGFR9F | GCGGGGCCATCGGCCCGGCTTGGCCTCCGACTTCCNNNNNGACGGGTTTCCTCTTCCTCCTC(9) |
| EGFR10F | CGGCGGCCTTGGGCCGGGCTTGGCCTCCGACTTCCNNNNNCTCTGAGTGCATACAGTGCCAC(10) |
| EGFR11F | GCCGCGCCTTCCGGCCCGCTTGGCCTCCGACTTCCNNNNNACTGTTTTTTCTCATTCCTTCC(11) |
| EGFR12F | GCGCCGCGATGCCCGGGGCTTGGCCTCCGACTTCCNNNNNGCCCAAAGTTCCGTGAGTTGAT(12) |
| EGFR13F | CCGCGGGGTAGCGCCCGGCTTGGCCTCCGACTTCCNNNNNACGTCTTCCTTCTCTCTCTGTC(13) |
| EGFR14F | GGCCGGCGTTGCGCCCGGCTTGGCCTCCGACTTCCNNNNNAAAGTTAAAATTCCCGTCGCTA(14) |
| EGFR15F | GCCCCGCGTTGGGCCGGCCTTGGCCTCCGACTTCCNNNNNTAACCTTCCCTCATTTCCTCCT(15) |
| EGFR16F | GCGCGCCGTTCGCGCGCGCTTGGCCTCCGACTTCCNNNNNGACAGCTTCTTGCAGCGATACA(16) |
| EGFR17F | CGGGGGGGTACCCGCGCCCTTGGCCTCCGACTTCCNNNNNCCTTCCTTTCATGCTCTCTTCC(17) |
| EGFR18F | CGCGCCGGTTGGCGCCCCCTTGGCCTCCGACTTCCNNNNNGCTCGTGCGTCCGAGCCTGTGG(18) |
| EGFR19F | GCGCGCGCTACGGCCGGGCTTGGCCTCCGACTTCCNNNNNCACAGGGAACCTTTGCTCTTTT(19) |
| EGFR20F | CGGGGGGGTAGGGCGGCCCTTGGCCTCCGACTTCCNNNNNAGTGCTCCGGGCGCTGCCGTGG(20) |
| EGFR21F | GCGGGCGCTTGGGCGCCGCTTGGCCTCCGACTTCCNNNNNTGTCTCTGTGTTCTTGTCCCCC(21) |
| EGFR22F | CGGGGGCCATGGGGCGCCCTTGGCCTCCGACTTCCNNNNNGGAGAAGCTCCCAACCAAGCTC(22) |
| EGFR23F | GCCGCGCTTGCCCGGCGCTTGGCCTCCGACTTCCNNNNNAATACACGTCTCTCTTATCTCT(23) |
| EGFR24F | CGGCGCGCATCGCGCGGGCTTGGCCTCCGACTTCCNNNNNAATTTAAAGACTCACTCTCCAT(24) |
| EGFR25F | GCCCCCCGTTCCCGGGGGCTTGGCCTCCGACTTCCNNNNNTGCTGTGACCCACTCTGTCTCC(25) |
| EGFR26F | CCGCGCGCTTCCGCGGCGCTTGGCCTCCGACTTCCNNNNNGTCTGCCATGCCTTGTGCTCCC(26) |
| EGFR27F | CCCCCGGCTTCGCGCGCGCTTGGCCTCCGACTTCCNNNNNCGGAGCCCAGGGACTGCGTCTC(27) |
| EGFR28F | GCGGCGGGTTCCGCGGGCTTGGCCTCCGACTTCCNNNNNCTCACCGCAGTTCCATTCTCCC(28) |
| EGFR29F | CGGCGCGCTACGGGGCGGCTTGGCCTCCGACTTCCNNNNNGCCGTGCGGTTCAGCAACAACC(29) |
| EGFR30F | CGGCCGGCATCGCGCCCCCTTGGCCTCCGACTTCCNNNNNAGAGCATCCAGTGGCGGGACAT(30) |
| EGFR31F | GCCGCCCCTACGGCCGCGCCTTGGCCTCCGACTTCCNNNNNCCCAGCGTGTCCTCTCTCCTCC(31) |
| EGFR32F | CGCCCCCCATGGGGCGGCCTTGGCCTCCGACTTCCNNNNNCCGAGACGAAGCCACGTGCAAG(32) |
| EGFR33F | GCGCCGGCTACCCGCGGGCTTGGCCTCCGACTTCCNNNNNATGCTCTACAACCCCACCACGT(33) |
| EGFR34F | CCGCCGCCTTCCCGGCCGCTTGGCCTCCGACTTCCNNNNNTTCCTTGTTCCTCCACCTCATT(34) |
| EGFR35F | CGGCGCCGTACGGCCGCCCTTGGCCTCCGACTTCCNNNNNCCATCGCCACTGGGATGGTGGG(35) |
| EGFR36F | GCCGGCGCTACGGCGCGCCCTTGGCCTCCGACTTCCNNNNNGGTGGTGGCCCTGGGGATCGGC(36) |
| EGFR37F | CGCGCGGCTACGCCGCCCCCTTGGCCTCCGACTTCCNNNNNCTTCTTTTCTTGCTTCATCCTC(37) |

TABLE 1-continued

Primer sequence information

| Sequence No. | Sequence (5'-3', SEQ ID NO:) |
|---|---|
| EGFR38F | CGCGCGGCATCGGCCGCCCTTGGCCTCCGACTTCCNNNNNGAGTTGATGACCTTTGGATCCA(38) |
| EGFR39F | CGCCGGCCATGGCCCCGCCTTGGCCTCCGACTTCCNNNNNCTGCCAGCGAGATCTCCTCCAT(39) |
| EGFR40F | GCCGGGCCTACCGGGGCCCTTGGCCTCCGACTTCCNNNNNATGTGATATCTGTCTTTTTCTT(40) |
| EGFR41F | CGCCCCCATCCCCGCGCCTTGGCCTCCGACTTCCNNNNNCAAGCTCACGCAGTTGGGCACT(41) |
| EGFR42F | CGCCCGGGTTGGCCGGCCCTTGGCCTCCGACTTCCNNNNNAGCCTCCAGAGGATGTTCAATA(42) |
| EGFR43F | CGGGCCCGTTGGGCGGCGCTTGGCCTCCGACTTCCNNNNNTCACAGCAGGGTCTTCTCTGTT(43) |
| EGFR44F | GGGCGCGGTTCCGCCCGCCTTGGCCTCCGACTTCCNNNNNACCGTCGCTTGGTGCACCGCGA(44) |
| EGFR45F | CGGGCCCGTTCCGCGCGCCTTGGCCTCCGACTTCCNNNNNACTGGTGAAAACACCGCAGCAT(45) |
| EGFR46F | GCCCGCGCTAGGCGCCGGCTTGGCCTCCGACTTCCNNNNNGAACATTTTTCTCCACCTTGGT(46) |
| EGFR47F | GCGCGCCGATGCCCGCCCCTTGGCCTCCGACTTCCNNNNNAGTGTGCCCACTACATTGACGG(47) |
| EGFR48F | GCGGCCCCTTGCCCCGGCCTTGGCCTCCGACTTCCNNNNNCTGCCCGGCAGGAGTCATGGGA(48) |
| EGFR49F | GCCGCGGCATCGCCCGGGCTTGGCCTCCGACTTCCNNNNNTAATAGCCTCAAAATCTCTGCA(49) |
| EGFR50F | GCGCCCGCTTCCCCCCCGCTTGGCCTCCGACTTCCNNNNNTGCCAAGTCCTACAGACTCCAA(50) |
| EGFR51F | GGCGCGCCTTCCCCGGGCCTTGGCCTCCGACTTCCNNNNNGGATGAAGAAGACATGGACGAC(51) |
| EGFR52F | CCCCCCGCATGCCGGCCCCTTGGCCTCCGACTTCCNNNNNCACGCATTTATGTTTTCTCTTC(52) |
| EGFR53F | GCGCCGGCATCGCCGGCCCTTGGCCTCCGACTTCCNNNNNCCCTCAACACAGTGGAGCGAAT(53) |
| EGFR54F | CCCCGGCGTACGGCGCCCCTTGGCCTCCGACTTCCNNNNNGATCATCAGAGGAAATATGTAC(54) |
| EGFR55F | CCCGGCGCTTCCGCCGCCTTGGCCTCCGACTTCCNNNNNACTGACGTGCCTCTCCCTCCCT(55) |
| EGFR56F | CGCGCGGCTACGGGCGGGCTTGGCCTCCGACTTCCNNNNNACGTGTGCCGCCTGCTGGGCAT(56) |
| EGFR57F | GCCGCCGGATGGGCCCGCCTTGGCCTCCGACTTCCNNNNNGCAGCTCATCACGCAGCTCATG(57) |
| EGFR58F | CCCGGCCCTTGGGGCCGCCTTGGCCTCCGACTTCCNNNNNCATGATTTTTCTTCTCTCCAAT(58) |
| EGFR59F | GGGGGCCGTTCCCCCGCCCTTGGCCTCCGACTTCCNNNNNATAACATCCTTGGGATTACGCT(59) |
| EGFR60F | GCGGGGCGTAGGCCCGCCCTTGGCCTCCGACTTCCNNNNNATGGAGATGTGATAATTTCAGG(60) |
| EGFR61F | GCCGCGGGTTGGGGCGCGCTTGGCCTCCGACTTCCNNNNNCACCTCTGATTTCTTTCCACTT(61) |
| EGFR62F | CCCCCCCCTACGGCCCGGCTTGGCCTCCGACTTCCNNNNNTGGCTCTGTGCAGAATCCTGTC(62) |
| EGFR63F | CGGGGGCCATCCCCGCCCCTTGGCCTCCGACTTCCNNNNNCCCACACTACCAGGACCCCCAC(63) |
| EGFR64F | CCGGGGCCTTCGGGGCGCTTGGCCTCCGACTTCCNNNNNCCAGCCCACCTGTGTCAACAGC(64) |
| EGFR65F | GCCGCGCGTTCGGCGCCGCTTGGCCTCCGACTTCCNNNNNCCACCAAATTAGCCTGGACAAC(65) |
| EGFR66F | CCGCGGGGTACGCGGGGGCTTGGCCTCCGACTTCCNNNNNGCCAAATGGCATCTTTAAGGGC(66) |
| EGFR1R | GCGCCCCCAACCGCCCC*TGGCTACGATCCGACTTGG*NNNNNGACACAGAGCTGTGAACACTTA(67) |
| EGFR2R | GGCGGCGCATCCGGCCGGTGGCTACGATCCGACTTGGNNNNNGCTTATAAGGTGTTCATACATA(68) |
| EGFR3R | GGGGCCCGCATCGCGGCGCTGGCTACGATCCGACTTGGNNNNNTCTGAGGCTGTTCACTGACTTA(69) |
| EGFR4R | CGCGCCGCAACCGCCCCGTGGCTACGATCCGACTTGGNNNNNTCATGTGATAATTCAGCTCAAA(70) |
| EGFR5R | GGCCCCGGATGGGGCCCGTGGCTACGATCCGACTTGGNNNNNTTAGCATCAGGATTATGACTCA(71) |
| EGFR6R | GGCCCCCGAACGCGCCCCTGGCTACGATCCGACTTGGNNNNNGAGCCGGCGAGACACGCCCTTA(72) |
| EGFR7R | GCGCGGCCAACGGGGCCCTGGCTACGATCCGACTTGGNNNNNTATGATTTCTAGGTTCTCAAAG(73) |
| EGFR8R | CCGGCCCGAACGGGCGCCTGGCTACGATCCGACTTGGNNNNNGCTTTGGCTGTGGTCAACTTAC(74) |

TABLE 1-continued

Primer sequence information

| Sequence No. | Sequence (5'-3', SEQ ID NO:) |
|---|---|
| EGFR9R | CCGGGCCGATGGCCCCGCTGGCTACGATCCGACTTGGNNNNNNTCATGGCCTGAGGCAGGCACTC(75) |
| EGFR10R | CCCGGCCCAAGGCCGCCGTGGCTACGATCCGACTTGGNNNNNNGATAGCAGCAAGGGGCTCTTAC(76) |
| EGFR11R | CGGGCCGGAAGGCGCGGCTGGCTACGATCCGACTTGGNNNNNNTCGGGCCATTTTGGAGAATTCG(77) |
| EGFR12R | CCCCGGGCATCGCGGCGCTGGCTACGATCCGACTTGGNNNNNNAAGCACAGACTGCAATTTGTAC(78) |
| EGFR13R | CCGGGCGCTACCCCGCGGTGGCTACGATCCGACTTGGNNNNNNGATGTTGCTTCTCTTAATTCCT(79) |
| EGFR14R | CCGGGCGCAACGCCGGCCTGGCTACGATCCGACTTGGNNNNNNACACAGCAAAGCAGAAACTCAC(80) |
| EGFR15R | GCCGGCCCAACGCGGGGCTGGCTACGATCCGACTTGGNNNNNNGTCAAGGCGCCTGTGGGGTCTG(81) |
| EGFR16R | CGCGCGCGAACGGCGCGCTGGCTACGATCCGACTTGGNNNNNNTGTTTCCAGACAAGCCACTCAC(82) |
| EGFR17R | GGCGCGGGTACCCCCCCGTGGCTACGATCCGACTTGGNNNNNNTCCTCCATCTCATAGCTGTCG(83) |
| EGFR18R | GGGGCGCCAACCGGCGCGTGGCTACGATCCGACTTGGNNNNNNCGCACACCGGCGGGCTTCCTAC(84) |
| EGFR19R | CCCGGCCGTAGCGCGCGCTGGCTACGATCCGACTTGGNNNNNNGTGGCAGCAGTCACTGGGGGAC(85) |
| EGFR20R | GGCCGCCCTACCCCCCCGTGGCTACGATCCGACTTGGNNNNNNGGCTGCTGGAGGGGCATCTTAC(86) |
| EGFR21R | CGGCGCCCAAGCGCCCGCTGGCTACGATCCGACTTGGNNNNNNTCAGTTTCCTTCAAGATCCTCA(87) |
| EGFR22R | GGCGCCCCATGGCCCCCGTGGCTACGATCCGACTTGGNNNNNNAGGCCTGTGCCAGGGACCTTAC(88) |
| EGFR23R | GCCGGGCAAGCCGCGGCTGGCTACGATCCGACTTGGNNNNNNGAAGTGTTTAATATTCGTAGCA(89) |
| EGFR24R | CCCGCGCGATGCGCGCCGTGGCTACGATCCGACTTGGNNNNNNAGCAACTGAACCTGTGACTCAC(90) |
| EGFR25R | CCCCCGGGAACGGGGGGCTGGCTACGATCCGACTTGGNNNNNNGGCTCCGGGCCCCAGCAGCCCT(91) |
| EGFR26R | CGCCGCGGAAGCGCGCGGTGGCTACGATCCGACTTGGNNNNNNCCTGCCTCGGCTGACATTCCGG(92) |
| EGFR27R | CGCGCGCGAAGCCGGGGGTGGCTACGATCCGACTTGGNNNNNNGATTAAAGAAATAACCTCCTAC(93) |
| EGFR28R | CCCGGCGGAACCCGCCGCTGGCTACGATCCGACTTGGNNNNNNATGCTCTCCACGTTGCACAGGG(94) |
| EGFR29R | CCGCCCCGTAGCGCGCCGTGGCTACGATCCGACTTGGNNNNNNGTTGCTGAGAAAGTCACTGCTG(95) |
| EGFR30R | GGGGCGCGATGCCGGCCGTGGCTACGATCCGACTTGGNNNNNNATAGTGTGTATGCGACACTTAC(96) |
| EGFR31R | GGCGGCCGTAGGGGCGGCTGGCTACGATCCGACTTGGNNNNNNAGAGCATGAGTGGGGGGCAGGT(97) |
| EGFR32R | GCCGCCCCATGGGGGGCGTGGCTACGATCCGACTTGGNNNNNNCCCTCGGGGTTCACATCCATCT(98) |
| EGFR33R | CCCGCGGGTAGCCGGCGCTGGCTACGATCCGACTTGGNNNNNNGGGCCCACAGAGGAGGACTCAC(99) |
| EGFR34R | CGGCCGGGAAGGCGGCGGTGGCTACGATCCGACTTGGNNNNNNCACCACCAGCAGCAAGAGGAGG(100) |
| EGFR35R | GGCGGCCGTACGGCGCCGTGGCTACGATCCGACTTGGNNNNNNCGATGTGGCGCCTTCGCATGAA(101) |
| EGFR36R | GCGCGCCGTAGCGCCGGCTGGCTACGATCCGACTTGGNNNNNNCCCACCCAGGACTGGCACTCAC(102) |
| EGFR37R | GGGCGGCGTAGCCGCGCGTGGCTACGATCCGACTTGGNNNNNNCTGGCAGGGATTCCGTCATATG(103) |
| EGFR38R | GGCGGCCGATGCCGCGCGTGGCTACGATCCGACTTGGNNNNNNAGGGAGGCGTTCTCCTTTCTCC(104) |
| EGFR39R | GCGGGCCATGGCCGGCGTGGCTACGATCCGACTTGGNNNNNNGACAGACCCACCAGTCACTCAC(105) |
| EGFR40R | GGCCCCGGTAGGCCCGGCTGGCTACGATCCGACTTGGNNNNNNGGAGGCTGAGAAAATGATCTTC(106) |
| EGFR41R | GCGCGGGATGGGGGCGTGGCTACGATCCGACTTGGNNNNNNAAATTCCCAAGGACCACCTCAC(107) |
| EGFR42R | GGCCGGCCAACCCGGGCGTGGCTACGATCCGACTTGGNNNNNNTAGGAAAATCAAAGTCACCAAC(108) |
| EGFR43R | CGCCGCCCAACGGGCCCGTGGCTACGATCCGACTTGGNNNNNNCACCAGTACGTTCCTGGCTGCC(109) |
| EGFR44R | GCGGGCGGAACCGCGCCCTGGCTACGATCCGACTTGGNNNNNNCCAGCCCAAAATCTGTGATCTT(110) |
| EGFR45R | GCGCGCGGAACGGGCCCGTGGCTACGATCCGACTTGGNNNNNNTGACCTAAAGCCACCTCCTTAC(111) |
| EGFR46R | CCGGCGCCTAGCGCGGGCTGGCTACGATCCGACTTGGNNNNNNCGGGCAGGTCTTGACGCAGTGG(112) |

TABLE 1-continued

Primer sequence information

| Sequence No. | Sequence (5'-3', SEQ ID NO:) |
|---|---|
| EGFR47R | GGGCGGGCATCGGCGCGCTGGCTACGATCCGACTTGGNNNNNACTTCCAGACCAGGGTGTTGTT(113) |
| EGFR48R | GCCGGGGCAAGGGGCCGCTGGCTACGATCCGACTTGGNNNNNTTCTCCTTCACTTTCCACTCAC(114) |
| EGFR49R | CCCGGGCGATGCCGCGGCTGGCTACGATCCGACTTGGNNNNNTTCATCCATCAGGGCACGGTAG(115) |
| EGFR50R | CGGGGGGGAAGCGGGCGCTGGCTACGATCCGACTTGGNNNNNTGAGGTACTCGTCGGCATCCAC(116) |
| EGFR51R | GCCCGGGGAAGGCGCGCCTGGCTACGATCCGACTTGGNNNNNGAGAGAGACAGAGATTTCATAC(117) |
| EGFR52R | GGGCCGGCATGCGGGGGGTGGCTACGATCCGACTTGGNNNNNGATGATCTGCAGGTTTTCCAAA(118) |
| EGFR53R | GGCCGGCGATGCCGGCGCTGGCTACGATCCGACTTGGNNNNNCTGCTAAGGCATAGGAATTTTC(119) |
| EGFR54R | GGGCGCCGTACGCCGGGGTGGCTACGATCCGACTTGGNNNNNCCTTGGCATCCCAGCCTCTCAC(120) |
| EGFR55R | GCCGGCGGAAGCGCCGGGTGGCTACGATCCGACTTGGNNNNNGAGCTGCACGGTGGAGGTGAGG(121) |
| EGFR56R | CCCGCCCGTAGCCGCGCGTGGCTACGATCCGACTTGGNNNNNCATAGTCCAGGAGGCAGCCGAA(122) |
| EGFR57R | GCGGGCCCATCCGGCGGCTGGCTACGATCCGACTTGGNNNNNCGTATCTCCCTTCCCTGATTAC(123) |
| EGFR58R | GCGGCCCCAAGGGCCGGGTGGCTACGATCCGACTTGGNNNNNTCTCCATCACTTATCTCCTTGA(124) |
| EGFR59R | GGCGGGGAACGGCCCCTGGCTACGATCCGACTTGGNNNNNATTTGCATAGCACAAATTTTTG(125) |
| EGFR60R | GGCGGGCCTACGCCCCGCTGGCTACGATCCGACTTGGNNNNNTAAACAGAAAGCGGTGACTTAC(126) |
| EGFR61R | CGCGCCCCAACCCGCGGCTGGCTACGATCCGACTTGGNNNNNCGGGGTTCAGAGGCTGATTGTG(127) |
| EGFR62R | CCGGGCCGTAGGGGGGGTGGCTACGATCCGACTTGGNNNNNACTCGGGGTTGCCCACTGCAGT(128) |
| EGFR63R | GGGCGGGGATGGCCCCCGTGGCTACGATCCGACTTGGNNNNNCCCAGTGGGCAGGGCTGTCGAA(129) |
| EGFR64R | CGCCCCCGAAGGCCCCGGTGGCTACGATCCGACTTGGNNNNNGAAAGAAGTCCTGCTGGTAGTC(130) |
| EGFR65R | CGGCGCCGAACGCGGCGCTGGCTACGATCCGACTTGGNNNNNGGTATTCTGCATTTTCAGCTGT(131) |
| EGFR66R | CCCCCGCGTACCCCGCGGTGGCTACGATCCGACTTGGNNNNNGGGCTCATACTATCCTCCGTGG(132) |

Note:
F: Forward primer; R: Reverse primer; "NNNNN": molecular tag.

For the forward primer, the 17 bp sequence "CTTGGCCTCCGACTTCC" (SEQ ID NO: 135) upstream of the molecular tag is a first universal sequence (refer to, for example EGFR1F, the first universal sequence is highlighted in italicized box), upstream sequence of the first universal sequence is a first random sequence, and downstream sequence of the molecular tag is a first specific sequence.

For the reverse primer, the 19 bp sequence "TGGCTACGATCCGACTTGG" (SEQ ID NO: 136) upstream of the molecular tag is a second universal sequence (refer to, for example EGFR1R, the second universal sequence is highlighted in italicized box), upstream sequence of the second universal sequence is a second random sequence, and downstream sequence of the molecular tag is a second specific sequence.

2. Experimental Steps

Figure 4:
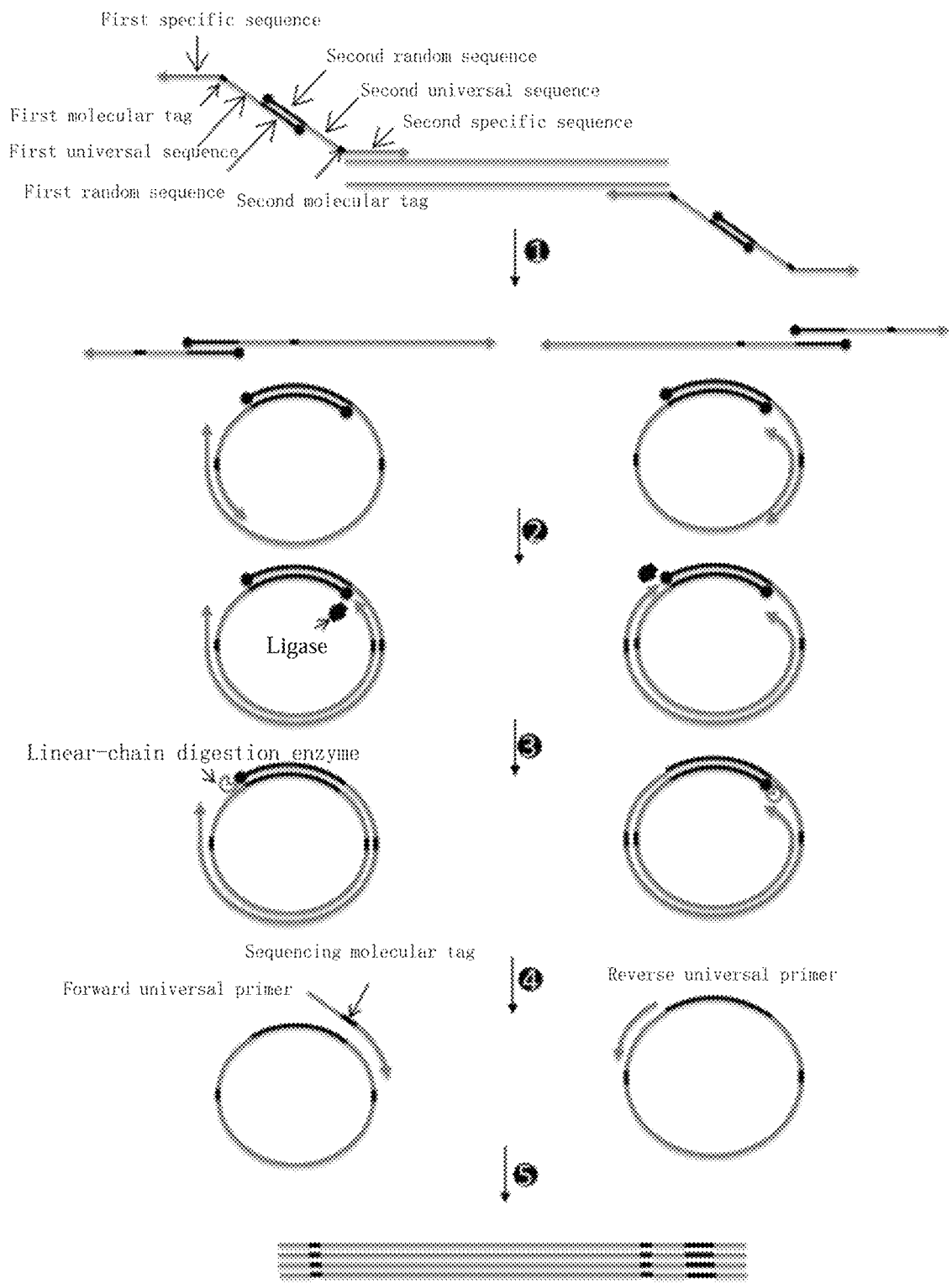
FIG. 4 is a schematic flow chart showing preparation of a BGISEQ-500 library by using a PCR primer pair of the present disclosure according to an embodiment of the present disclosure.

For a positive standard, a negative standard and a fresh tissue sample predicted without mutation, mutation in exon region of EGFR gene in these samples was detected respectively, in which the positive standard and the negative standard (i.e. Tru-Q 7 Reference Standard, Catalog No: HD734) are genomic DNAs commercially available from Horizon, and the fresh tissue sample is Yanhuang cell line-genomic DNAs. Referring to FIG. 4, a target region (that is, exon region sequence of EGFR gene) was enriched by the method for enriching a target region sequence of a DNA sample to be tested according to the present disclosure, with each experiment performed in duplicate.

2.1 Multiplex PCR Amplification 10 ng of the positive standard, the negative standard and the Yanhuang cell line-genomic DNAs taken were respectively subjected to multiplex PCR amplification according to the amplification system as follows:

| | |
|---|---|
| Polymerase Buffer (10X) | 2 μL |
| Forward primer mixture | 0.5 μL |
| Reverse primer mixture | 0.5 μL |
| dNTP | 0.5 μL |
| Polymerase | 0.2 μL |
| DNA template | 0.2 μL |
| Water | 16.1 μL |
| Total | 20 μL |

Note: Forward and reverse primer pool was a mixture of all corresponding primers in Table 1 in an equal proportion.

The amplification conditions for multiplex PCR amplification were as follows:

| | |
|---|---|
| step 1 | 98° C., 2 minutes |
| step 2 | 98° C., 10 seconds |
| step 3 | 58° C., 5 minutes |
| step 4 | 72° C., 30 seconds |
| step 5 | 98° C., 10 seconds |
| step 6 | 72° C., 15 minutes |
| step 7 | 72° C., 5 minutes |
| step 8 | holding at 16° C. |

2.2 Ligation Reaction

For each sample, the amplification products obtained in the step 2.1 were subjected to a ligation reaction according to the reaction system shown in the following table:

| | |
|---|---|
| Previous amplification product | 20 μL |
| DNA ligase | 5 μL |
| 10X buffer | 3 μL |
| Distilled water | 2 μL |
| Total | 30 μL |

Reaction condition was 37° C. for 30 minutes.

Thus, a ligation product was obtained, and the ligation product was circular DNAs.

2.3 Linear-Chain Digestion Reaction

Linear DNAs (such as residual primers, non-specific products and the like) in the ligation product of each sample obtained in the step 2.2 were subjected to a linear-chain digestion reaction according to the reaction system shown in the following table:

| | |
|---|---|
| Mixture of ligation reaction | 32 μL |
| EXO I | 2 μL |
| EXO III | 1 μL |
| Total | 35 μL |

Reaction condition was 37° C. for 30 minutes.

The resulting product after digestion was purified by XP magnetic beads, and the purified DNAs were dissolved in 17 μL of distilled water, for use.

2.4 PCR Enrichment of Circular Products

The resulting product of each sample obtained in the step 2.3 was subjected to PCR enrichment according to the reaction system as shown in the following table:

| | |
|---|---|
| Polymerase buffer (10X) | 2 μL |
| Forward universal primer | 0.5 μL |
| Reverse universal primer | 0.5 μL |
| dNTP | 0.5 μL |
| Polymerase | 0.2 μL |
| DNA template | 16.3 μL |
| Total | 20 μL |

The forward universal primer is of a nucleotide sequence of (SEQ ID NO: 133)
5'-TGTGAGCCAAGGAGTTGAAGTGGCGCATTGTCTTCCTAAGACC CTTGGCCT CCGACTTCC -3', in which the sequence of sequencing tag is underlined, and sequence in the box is same as the first universal sequence.

The reverse universal primer is of a nucleotide sequence of (SEQ ID NO: 134)
5'-phos/GAACGACA TGGCTACGATCCGACTTGG -3', in which sequence in the box is same as the second universal sequence.

Figure 5:
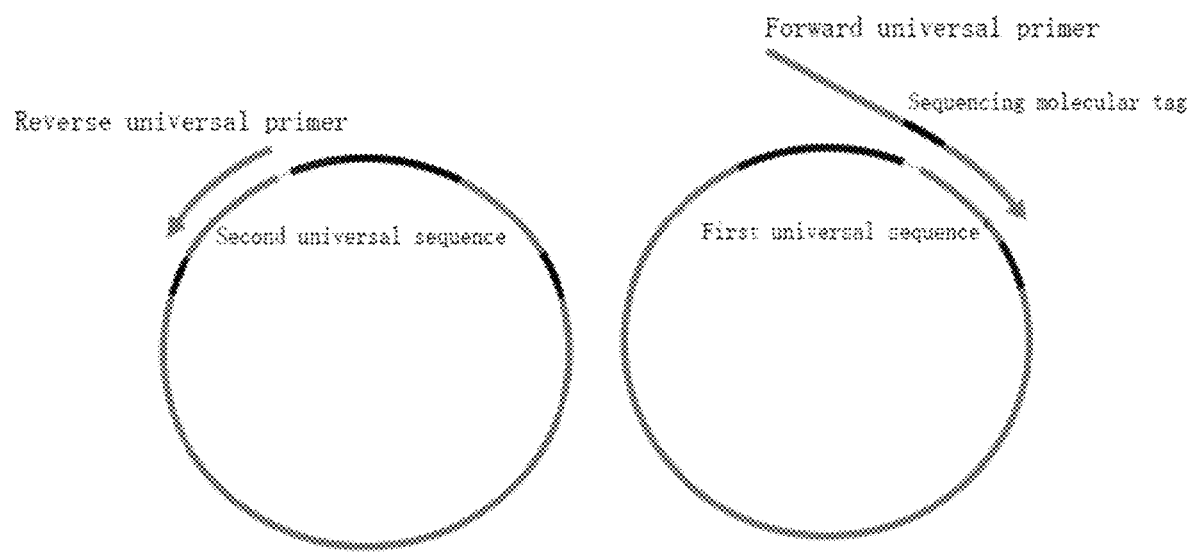
FIG. 5 is a schematic diagram showing binding between PCR amplification product containing a universal sequence and universal primer according to an embodiment of the present disclosure.

The schematic diagram showing binding between forward and reverse universal primers and universal sequences is shown in FIG. 5.

The condition for PCR reaction was as follows:

| step 1 | 98° C., 2 minutes |
|---|---|
| step 2 | 98° C., 10 seconds |
| step 3 | 58° C., 30 minutes |
| step 4 | 72° C., 30 seconds |
| step 5 | repeating steps 3 and 4 for 32 cycles |
| step 6 | 72° C., 5 minutes |
| step 7 | holding at 16° C. |

Thus, the enriched product of each sample was obtained, that is, a sequencing library.

After that, the enriched products were subjected to purification by XP magnetic beads. The purified DNAs were dissolved in 30 μL of distilled water, followed by 2100 electrophoresis detection, with electrophoresis detection results shown in FIG. 6.

2.5 On-Machine Sequencing

The qualified library was subjected to on-machine sequencing by using BGISEQ-500 sequencing platform based on paired-end sequencing, 50 bp of sequencing length and 10 bp of sequencing tag length (i.e. PE50+10).

2.6 Data Analysis

The obtained sequencing results were subjected to data analysis, specifically including: filtering off-machine sequencing reads, such that the reads having base quality less than 10 were removed, thus ensuring high quality for the data used for base frequency analysis; aligning the filtered clean reads to the human genome reference sequence HG19 (GRCH37) through alignment software bwa (V0. 7.7-r441); removing repeats and errors via half of molecular tags in amplicon followed by statistical analysis of coverage depth of 4 bases (ATCG) at sites to be detected based on the alignment results, and thus obtaining information such as most-likely mutation site and frequency thereof, sequencing error and frequency thereof and the like via the coverage depth; performing GC bias correction according to GC distribution in regions (where the mutation site and primer were presented), as well as the likely frequency of sequencing error; and detecting the mutation sites obtained as above by using the mutation detection tool GATK (V3.6) which is most accurate currently; and filtering and annotating through the corresponding mutation database.

As a result, the present inventors have found that it is possible to accurately detect mutations as low as 0.1% by using the PCR primer pair of the present disclosure for multiplex PCR amplification and library construction. Specifically, four sites in EGFR of the positive standard, respectively having 16.7%, 1.0%, 1.0%, 1.0% and 1.0% of theoretical mutation rate, are detected to have a mutation rate of 16.6%, 0.6%, 1.0%, 0.8% and 1.1% respectively according to the present disclosure, indicating that positive samples can be detected correctly; and the negative standard and Yanhuang samples are respectively detected to have 0.0% of mutation rate in EGFR, referring to Table 3 to Table 5. In addition, the method of the present disclosure displays good specificity, with 98-99% of alignment rate, 96-97% of capture efficiency and 100% of coverage (refer to Table 2); is of good homogeneity, obtaining 0.1× average depth greater than 95%, indicating no significant difference in depth between amplicons (refer to FIG. 7); and has good stability, as well as few differences between different samples (refer to FIG. 8).

TABLE 2

PE50 + 10 off-machine data

| Serial Nos. | Original data | Alignment rate | Capture efficiency | Coverage | Homogeneity* |
|---|---|---|---|---|---|
| 1 | 592423 | 99.2% | 98.6% | 100% | 94.6% |
| 2 | 534193 | 98.8% | 98.5% | 100% | 95.4% |
| 3 | 624015 | 99.1% | 98.2% | 100% | 95.4% |

*Homogeneity: ratio of amplicons greater than 0.1X average depth to total amplicons

TABLE 3

Mutation rate detected in positive standard

| Gene | Mutation types | Theoretical mutation rate | Detected mutation rate |
|---|---|---|---|
| EGFR | G719S | 16.7% | 16.6% |
| EGFR | L858R | 1.0% | 0.6% |
| EGFR | L861Q | 1.0% | 1.0% |
| EGFR | T790M | 1.0% | 0.8% |
| EGFR | ΔE746-A750 | 1.0% | 1.1% |

TABLE 4

Mutation rate detected in negative standard

| Gene | Mutation types | Theoretical mutation rate | Detected mutation rate |
|---|---|---|---|
| EGFR | G719S | 0.0% | 0.0% |
| EGFR | L858R | 0.0% | 0.0% |
| EGFR | L861Q | 0.0% | 0.0% |
| EGFR | T790M | 0.0% | 0.0% |
| EGFR | ΔE746-A750 | 0.0% | 0.0% |

TABLE 5

Mutation rate detected in Yanhuang sample

| Gene | Mutation types | Predicted mutation rate | Detected mutation rate |
|---|---|---|---|
| EGFR | G719S | 0.0% | 0.0% |
| EGFR | L858R | 0.0% | 0.0% |
| EGFR | L861Q | 0.0% | 0.0% |
| EGFR | T790M | 0.0% | 0.0% |
| EGFR | ΔE746-A750 | 0.0% | 0.0% |

Figure 6:
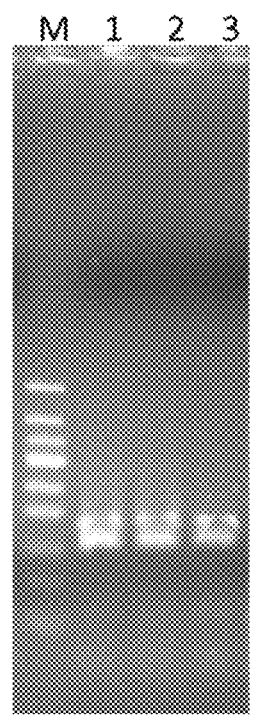
FIG. 6 is a graph showing detection results of 2100 electrophoresis of libraries of different samples obtained in Example 1.
Figure 7:
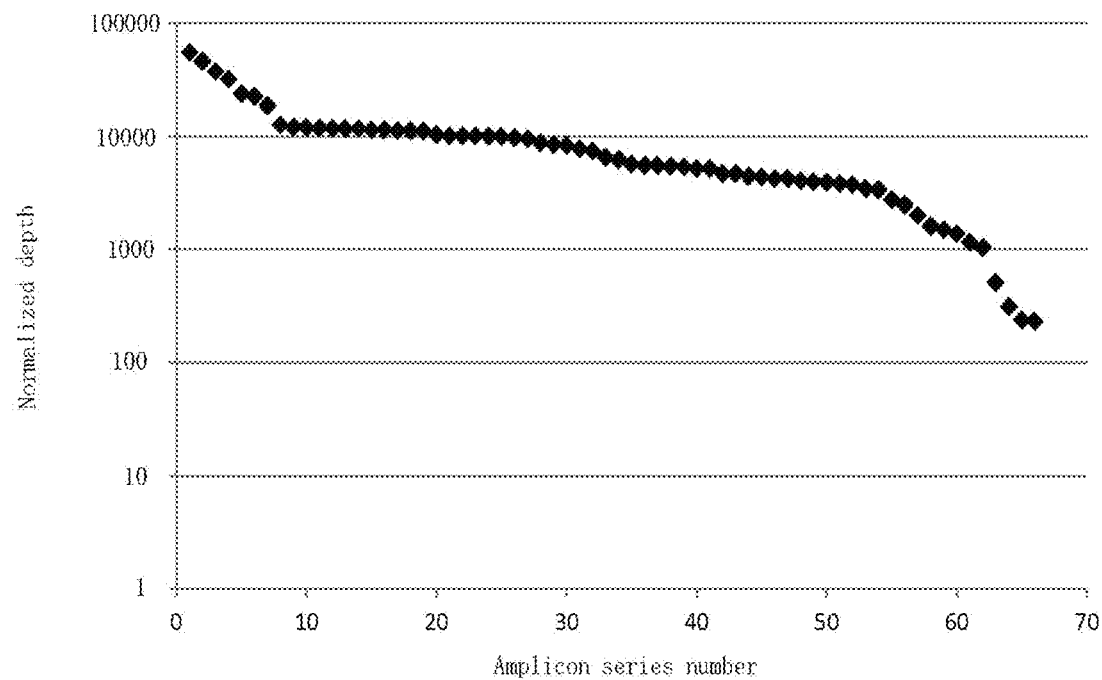
FIG. 7 is a graph showing homogeneity detection results of sequencing data obtained in Example 1.
Figure 8:
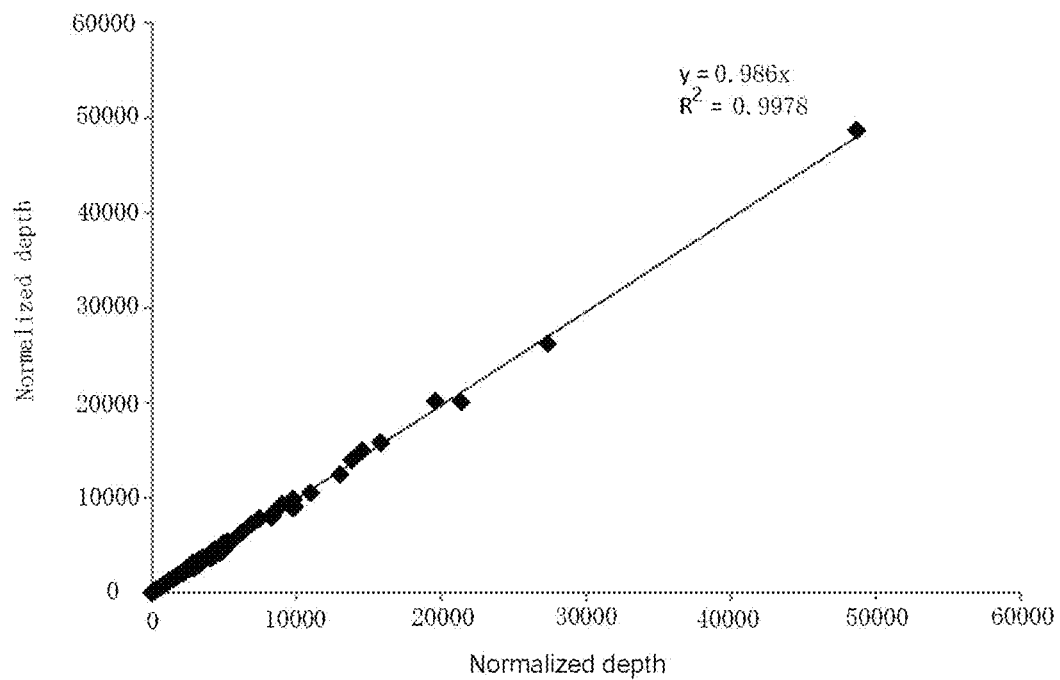
FIG. 8 is a graph showing stability detection results of sequencing data obtained in Example 1.

FIG. 6 shows the electrophoresis detection results of enriched products of samples, i.e. of BGISEQ-500 libraries. As shown in FIG. 6, bands 1, 2 and 3 are respectively electrophoresis detection results of libraries of the positive standard, the negative standard and the Yanhuang cell line-genomic DNAs obtained through circular multiplex PCR, each library having a length of 150-200 bp. FIG. 7 shows the coverage depth of different amplicons based on sequencing data, that is, homogeneity test results. As shown in FIG. 7, the X-axis refers to the amplicon series number and the Y-axis refers to the depth of coverage. FIG. 8 shows the stability test results of sequencing data, that is, comparison of depth of same region in a same sample obtained by different experiments. As shown in FIG. 8, the X-axis and the Y-axis each refer to normalized coverage depth.

In addition, the present inventors also performed a series of experiments, and have discovered that the PCR primer pair and the method for enriching a target region sequence of the present disclosure is useful not only for genomic DNA samples, but also widely for samples like cfDNA, FFPE, urine DNA, fresh frozen sample and the like; and can be applied for constructing both BGI-Seq library and libraries for other sequencing platforms, such as illumina, proton and the like.

INDUSTRIAL APPLICABILITY

The PCR primer pair of the present disclosure can be effectively used for PCR amplification of DNA samples to be tested, effectively reduce GC bias during PCR amplification, and improve amplification specificity. Further, the amplified products can be enriched conveniently.

Although specific embodiments of the present disclosure have been described in detail, it would be appreciated by those skilled in the art that various modifications and alternatives of the details can be made according to teachings of the present disclosure, which are all within the scope of the present disclosure. The full scope of the present disclosure is given by the appended claims and any equivalents thereof.

Reference throughout this specification to terms "an embodiment", "some embodiments", "illustrative embodiment", "an example", "a specific example" or "some examples" means that a particular feature, structure, material, or characteristic described in connection with the embodiment or example is included in at least one embodiment or example of the present disclosure. Thus, the description with reference to the terms "an embodiment", "some embodiments", "illustrative embodiment", "an example", "a specific example" or "some examples" throughout this specification are not necessarily referring to the same embodiment or example of the present disclosure. Furthermore, the particular features, structures, materials, or characteristics may be combined in any suitable manner in one or more embodiments or examples.

What is claimed is:

1. A PCR primer pair, comprising a first primer and a second primer, wherein
the first primer comprises a first specific sequence, a first random sequence and a first universal sequence, and
the second primer comprises a second specific sequence, a second random sequence and a second universal sequence, wherein
the first specific sequence is located at the 3' end of the first primer, the first random sequence is located at the 5' end of the first primer, and the first universal sequence is located between the first specific sequence and the first random sequence,
the second specific sequence is located at the 3' end of the second primer, the second random sequence is located at the 5' end of the second primer, and the second universal sequence is located between the second specific sequence and the second random sequence,
wherein the first specific sequence and the second specific sequence are respectively an upstream primer and a downstream primer for a target sequence, and
the first random sequence and the second random sequence are reversely complementary.

2. The PCR primer pair according to claim 1, wherein the first specific sequence and the second specific sequence each have a TM value of 55-65° C., and
the first primer and the second primer each have a TM value of 65-75° C.

3. The PCR primer pair according to claim 1, wherein
the first random sequence and the second random sequence each have a length of 15-45 bp, and
the first specific sequence and the second specific sequence each have a length of 15-30 bp.

4. The PCR primer pair according to claim 1, wherein the 1-5$^{th}$ bases from each of the 5' end and the 3' end of the first primer are respectively subjected to thio-modification, and
the 1-5$^{th}$ bases from each of the 5' end and the 3' end of the second primer are respectively subjected to thio-modification.

5. The PCR primer pair according to claim 4, wherein the thio-modification is selected from phosphorothioate modification, methyl-sulfate modification and peptide nucleic acid modification.

6. The PCR primer pair according to claim 1, wherein at least one of the first primer and the second primer is subjected to phosphorylation modification at the 5' end.

7. The PCR primer pair according to claim 1, wherein the first primer further comprises a first molecular tag, and the first molecular tag is located between the first universal sequence and the first specific sequence, and
the second primer further comprises a second molecular tag, and the second molecular tag is located between the second universal sequence and the second specific sequence.

8. The PCR primer pair according to claim 7, wherein the first molecular tag and the second molecular tag have different sequences.

9. The PCR primer pair according to claim 7, wherein the first molecular tag and the second molecular tag each have a sequence in a length of 5-10 bp.

10. The PCR primer pair according to claim 1, wherein the first universal sequence and the second universal sequence each have a length of 15-20 bp.

* * * * *